United States Patent
Tao et al.

(10) Patent No.: US 11,020,189 B2
(45) Date of Patent: Jun. 1, 2021

(54) SYSTEM AND METHOD FOR COMPONENT POSITIONING BY REGISTERING A 3D PATIENT MODEL TO AN INTRA-OPERATIVE IMAGE

(71) Applicant: Radlink, Inc., El Segundo, CA (US)

(72) Inventors: Wenchao Tao, Los Angeles, CA (US); Brad L. Penenberg, Los Angeles, CA (US)

(73) Assignee: RADLINK, INC., El Segundo, CA (US)

( * ) Notice: Subject to any disclaimer, the term of this patent is extended or adjusted under 35 U.S.C. 154(b) by 0 days.

(21) Appl. No.: 16/900,629

(22) Filed: Jun. 12, 2020

(65) Prior Publication Data
US 2020/0305988 A1    Oct. 1, 2020

Related U.S. Application Data

(63) Continuation-in-part of application No. 16/212,065, filed on Dec. 6, 2018, and a continuation-in-part of
(Continued)

(51) Int. Cl.
*A61B 34/00* (2016.01)
*A61B 90/00* (2016.01)
(Continued)

(52) U.S. Cl.
CPC ............. *A61B 34/25* (2016.02); *A61B 34/10* (2016.02); *A61B 90/06* (2016.02); *A61B 90/39* (2016.02);
(Continued)

(58) Field of Classification Search
CPC ...................................................... G06T 7/33
See application file for complete search history.

(56) References Cited

U.S. PATENT DOCUMENTS

| 2019/0380792 A1* | 12/2019 | Poltaretskyi | ......... G06N 3/0454 |
| 2020/0275976 A1* | 9/2020 | Mckinnon | .............. A61B 34/20 |
| 2020/0405396 A1* | 12/2020 | Mcguan | ................. G06N 20/00 |

* cited by examiner

*Primary Examiner* — Oneal R Mistry
(74) *Attorney, Agent, or Firm* — Cislo & Thomas, LLP; Kelly W. Cunningham, Esq.

(57) ABSTRACT

The invention comprises a system and method that may help place or position a component, such as an acetabular cup or a femoral component, during surgery. An example system may iteratively register a plurality of two-dimensional projections from a three-dimensional model of a portion of a patient, the three-dimensional model being generated from a data set of imaging information obtained at a neutral position. An example system may further score each two-dimensional projection against an intra-operative image by calculating a spatial difference between corresponding points. A two-dimensional projection having a minimum score reflecting the smallest distance between the corresponding points may be identified. Using the two-dimensional projection having the minimum score, an adjustment score reflecting a difference in the values representing the orientation of the three-dimensional model at the intra-operative projection position and values representing the orientation of the three-dimensional model at the neutral position may be calculated. The invention also comprises a system and method also comprising surgical method and workflow to improve the efficiency of a surgical procedure by intraoperatively acquiring a digital radiographic image, processing the digital radiographic image, and using information based on the radiographic image to make adjustments during the surgical procedure. A checklist of parameters may be displayed so that the surgeon can confirm all considerations have been made for the surgical procedure.

23 Claims, 16 Drawing Sheets

Related U.S. Application Data application No. 15/133,999, filed on Apr. 20, 2016, now Pat. No. 10,743,945, which is a continuation-in-part of application No. 14/481,810, filed on Sep. 9, 2014, which is a continuation-in-part of application No. 13/633,799, filed on Oct. 2, 2012, now Pat. No. 8,831,324.

(51) Int. Cl.
*G06T 7/149* (2017.01)
*G06T 7/187* (2017.01)
*G06T 7/13* (2017.01)
*G06T 7/38* (2017.01)
*A61B 34/10* (2016.01)

(52) U.S. Cl.
CPC ............... G06T 7/13 (2017.01); G06T 7/149 (2017.01); G06T 7/187 (2017.01); G06T 7/38 (2017.01); *A61B 2034/102* (2016.02); *A61B 2034/105* (2016.02); *A61B 2034/252* (2016.02); *A61B 2090/061* (2016.02); *A61B 2090/067* (2016.02); *G06T 2207/10124* (2013.01); *G06T 2207/20152* (2013.01); *G06T 2207/30008* (2013.01); *G06T 2207/30052* (2013.01); *G06T 2211/424* (2013.01)

SYSTEM AND METHOD FOR COMPONENT POSITIONING BY REGISTERING A 3D PATIENT MODEL TO AN INTRA-OPERATIVE IMAGE

CROSS-REFERENCES TO RELATED APPLICATIONS

This patent application is a continuation-in-part application to U.S. patent application Ser. No. 16/212,065, filed Dec. 6, 2018, and a continuation-in-part application to U.S. patent application Ser. No. 15/133,999, filed Apr. 20, 2016, which is a continuation-in-part of U.S. patent application Ser. No. 14/481,810, filed Sep. 9, 2014, which is a continuation-in-part of U.S. patent application Ser. No. 13/633,799, filed Oct. 2, 2012, now U.S. Pat. No. 8,831,324.

The foregoing applications are incorporated herein in their entireties by this reference thereto.

TECHNICAL FIELD

This disclosure relates to a system and method for obtaining a proper placement and positioning of a component such as an acetabular cup or a femoral component during a surgical procedure.

BACKGROUND

Patients are often exposed to a series of x-ray radiation exposures during certain types of surgery, including during total hip arthroplasty and other orthopaedic procedures, because the patient may have to be placed in a desired position or orientation, moved around, and returned to the initial desired position during surgery. Furthermore, x-rays may be needed or desired to ensure proper placement of surgical components in the patient during surgery.

Repeated x-rays may be taken to assure that, after the patient is moved, any components are in an optimal position and/or that the patient is returned to the desired position to complete surgery.

X-rays may also be used to determine one or more target positioning values for a component before a surgery. While such pre-operative x-ray images may provide a surgeon with a general idea of the patient's anatomy and approximate positioning values for a component, differences in the patient placement and/or x-ray device placement relative to each other when x-ray images are produced at different times may introduce variations to x-ray images. These variations may, for example, hinder a surgeon from determining exact, proper positioning values for a component during a surgery while looking at an intra-operative x-ray image. It may take multiple x-rays to precisely establish a patient at the neutral position.

Similarly, post-operation x-rays may be taken to confirm proper placement of any components, implants, prostheses, etc. For the same reasons, it is important that the patient position be consistent with the pre-operation and intra-operation patient position to ensure consistent measurements.

At the same time, however, it may be undesirable, difficult, or impossible to return a patient to a neutral position, especially during a surgery or immediately after a surgery.

In many surgeries, consistent and accurate component placement may be critical. In total hip arthroplasty, for example, accurate placement of an acetabular cup may allow the acetabular cup to have a long life with little wear. Deviations in positioning values of an acetabular cup, including inclination, anteversion, and/or tilt may contribute to a reduced life of the acetabular cup, increase the risk of post-operative dislocation, and the like.

It is accordingly desirable to confirm placement of a component during surgery, where the surgeon may make any beneficial adjustments to the prosthesis while the patient is still opened up. The inability of many medical professionals to reproduce exact pre-operative x-ray conditions intra-operatively may presently limit the utility of intra-operative x-rays to confirm an accurate component placement, thus increasing the risk that the component is inaccurately placed and increasing the risk of associated negative outcomes for the patient. Similarly, it may be desired to minimize patient movement during surgery, especially if the movement is solely for the purpose of obtaining x-ray images.

There is a need for a surgical system and associated techniques that improve the accuracy and reproducibility of determining and confirming proper positioning values of a component while limiting the exposure of a patient to x-ray radiation. There is an additional need for a surgical system and associated techniques that allow x-ray images yielding accurate measurements to be taken while reducing or eliminating the need to place the patient in the neutral position.

SUMMARY

The present disclosure provides a system and method that may be useful to determine a proper placement of a component during a surgery, such as the proper placement of an acetabular cup during total hip arthroplasty. Similarly, the system and method of the present disclosure may be useful to measure a component position and accurately adjust the component if needed to achieve a target component placement. Before surgery, a surgeon or other medical personnel may obtain image data of a patient, such as three-dimensional ("3D") image information of a patient or a portion of a patient. 3D imaging information may be obtained using computed tomography ("CT"), magnetic resonance imaging ("MRI") or nuclear magnetic resonance imaging ("NMR"), and the like. Modern 3D imaging techniques and systems may be precise. 3D imaging techniques may produce volumetric data, or a 3D data set comprising series of 2D slices taken at regular intervals. Using the 3D data set of imaging information, a 3D model of the imaged patient or imaged portion of the patient may be obtained. From the 3D model, one or more two-dimensional ("2D") projections of the 3D model may be obtained. A 2D projection may simulate a more traditional radiographic image, such as an x-ray image.

As used herein, a "neutral position" refers to the position of the patient being imaged (or a portion of the patient being imaged) before substantively commencing surgery, often pre-operatively. Imaging information taken at a neutral position may be used as a reference point against which to compare later imaging information, such as intra-operative or post-operative imaging information. If spatial values are assigned to imaging information, imaging information (or one or more portions thereof) obtained at a neutral position may be defined as an origin.

An aspect of the present disclosure is directed to a method of positioning a component intra-operatively that includes the steps of iteratively registering a plurality of two-dimensional projections of a portion of a patient from a three-dimensional model of the portion of the patient, the three-dimensional model being generated from a data set of imaging information obtained at a neutral position, and each two-dimensional projection having a spatial orientation; scoring each two-dimensional projection against an intraoperative image by determining a best fit of each projection to the intra-operative image and calculating a spatial difference between corresponding points; identifying a global minimum score reflecting the smallest spatial difference between the corresponding points on the two-dimensional projection and the intra-operative image and selecting the two-dimensional projection having the global minimum score as an intra-operative projection; obtaining values representing the orientation of the three-dimensional model corresponding to the intra-operative projection; and calculating an adjustment factor based on the difference in the values representing the orientation of the three-dimensional model at the intra-operative projection position and values representing the orientation of the three-dimensional model at the neutral position.

An alternate aspect of the present disclosure is directed to a method for positioning a component intra-operatively including the steps of receiving a data set of imaging information representing at least a first portion of a patient in a neutral position; generating a three-dimensional model of the first portion of the patient based on the data set of imaging information; receiving intra-operative imaging information representing the first portion of the patient; identifying a bony edge contour in the intra-operative imaging information; iteratively rendering a plurality of two-dimensional projections from the three-dimensional model, each two-dimensional projection having a corresponding spatial orientation; scoring each two-dimensional projection by calculating the distance of the bony edge contour in the intra-operative imaging information to a corresponding contour in each two-dimensional projection and identifying a global minimum score; outputting a transformation matrix for the two-dimensional projection having the global minimum score, the transformation matrix representing the orientation of the three-dimensional model relative to the neutral position when the two-dimensional projection having the global minimum score was rendered; and calculating an adjustment factor based on the transformation matrix.

In an embodiment, an example method may include a step of outputting a visual indication of an intra-operative adjustment to be made to a component based on the adjustment factor to achieve a target component orientation. Alternatively, an example method may include a step of applying the adjustment factor to an intra-operative leg length measurement and outputting a visual indication of an intra-operative adjustment to be made to the patient to achieve a target leg length measurement. Alternatively or additionally, a component may be an acetabular cup, a femoral component, measurement device or aid, or another type of orthopaedic implant or prosthesis.

In an embodiment, an example method may include a step of scoring a first two-dimensional projection occurs before or during the step of registering a subsequent two-dimensional projection. Alternately, an example method may include registering each of the plurality of two-dimensional projections before scoring any two-dimensional projection.

In an embodiment, the data set of imaging information may be the result of a three-dimensional imaging procedure such as CT or MM. In an additional embodiment, the data set of imaging information may include volumetric imaging data. Further, in another embodiment, the three-dimensional model of the patient or the portion of the patient imaged may be generated by applying a region grow algorithm, a water shed algorithm, an active contour algorithm, or a combination thereof to the data set of imaging information.

Another aspect of the present disclosure is directed to an imaging system for intra-operatively positioning a component, the system including a computerized display system including a display, a receiver, and a microcontroller operatively coupled to the display and to the receiver and having access to system memory, the system memory including software instruction causing the microcontroller to perform the steps of: receiving a data set of imaging information representing at least a first portion of a patient in a neutral position; generating a three-dimensional model of the first portion of the patient based on the data set of imaging information; receiving intra-operative imaging information representing the first portion of the patient; identifying a bony edge contour in the intra-operative imaging information; iteratively rendering a plurality of two-dimensional projections from the three-dimensional model, each two-dimensional projection having a corresponding spatial orientation; scoring each two-dimensional projection by calculating the distance of the bony edge contour in the intra-operative imaging information to a corresponding contour in each two-dimensional projection and identifying a global minimum score; outputting a transformation matrix for the two-dimensional projection having the global minimum score, the transformation matrix representing the orientation of the three-dimensional model relative to the neutral position when the two-dimensional projection having the global minimum score was rendered; calculating an adjustment factor based on the transformation matrix; and outputting to the display a visual indication of an intra-operative adjustment to be made to a component based on the adjustment factor to achieve a target component orientation.

In an embodiment of the system, a component may be an acetabular cup, a femoral component, measurement device or aid, or another type of orthopaedic implant or prosthesis. In a specific embodiment of the system, the component may be an acetabular cup; and the visual indication may include an outline of the target component orientation; real-time inclination, anteversion, and tilt values of the component; target inclination, anteversion, and tilt values of the component; and/or combinations thereof.

BRIEF DESCRIPTION OF THE DRAWINGS

The foregoing and other features of the present disclosure will become more fully apparent from the following description and appended claims, taken in conjunction with the accompanying drawings. Understanding that these drawings depict several examples in accordance with the disclosure and are, therefore, not to be considered limiting of its scope, the disclosure is described with additional specificity and detail below through the use of the accompanying drawings.

DESCRIPTION OF THE PREFERRED EMBODIMENTS

Figure 1:
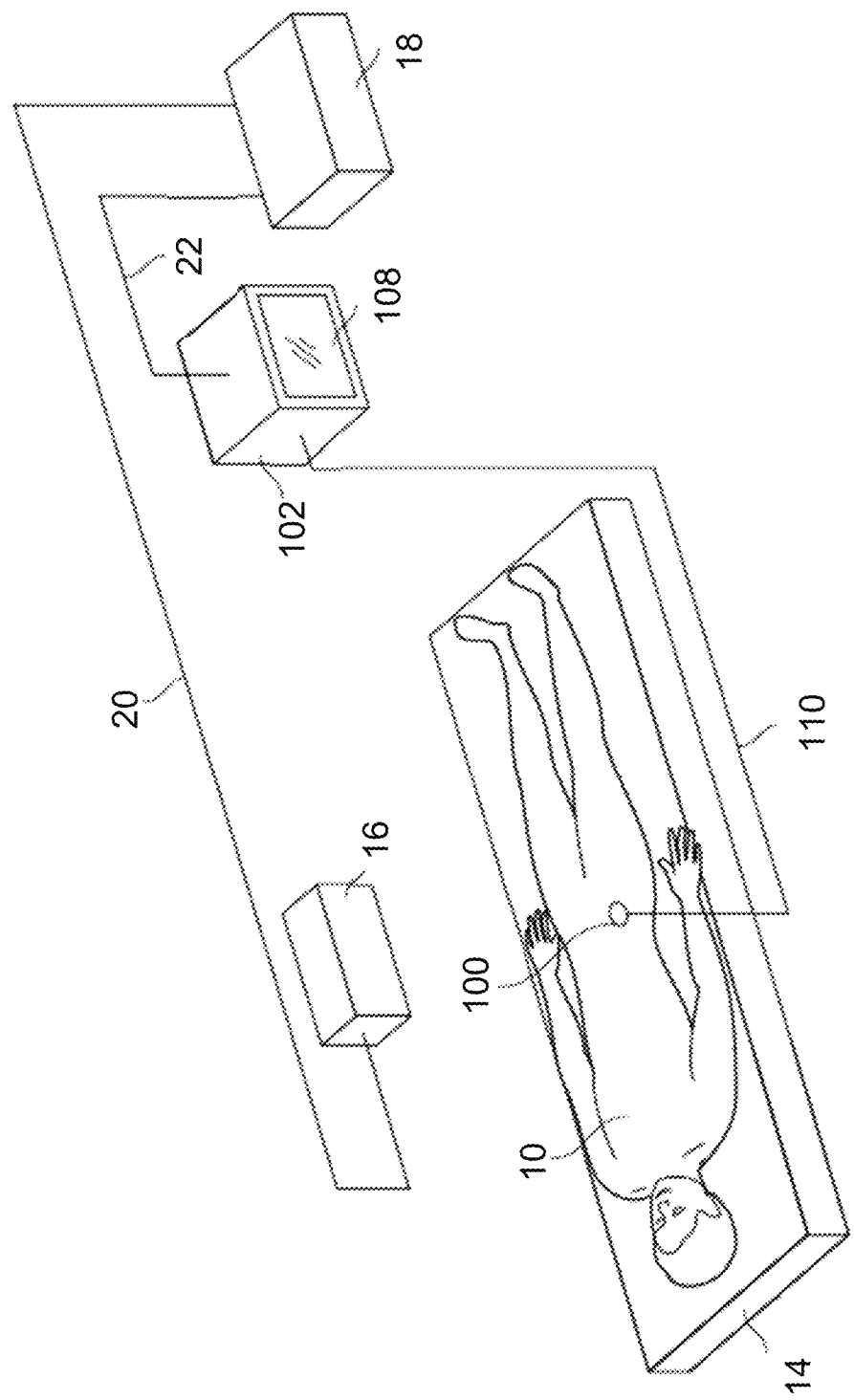
FIG. 1 is a block diagram view of an exemplary system and an associated patient and x-ray shows an embodiment of exemplary system architecture in accordance with an embodiment of the present disclosure.

The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

In the following detailed description, reference is made to the accompanying drawings, which form a part hereof. In the drawings, similar symbols identify similar components, unless context dictates otherwise. The illustrative examples described in the detailed description and drawings are not meant to be limiting and are for explanatory purposes. Other examples may be utilized, and other changes may be made, without departing from the spirit or scope of the subject matter presented herein. It will be readily understood that the aspects of the present disclosure, as generally described herein and illustrated in the drawings, may be arranged, substituted, combined, and designed in a wide variety of different configurations, each of which are explicitly contemplated and make part of this disclosure.

Referring to FIG. 1, a computerized surgery assist computer 102 may receive anatomic image information of a patient 10 or a portion of a patient 10 (e.g., a pelvis) taken by an anatomical scanning device, such as an x-ray scanner 16 (e.g., when receiving discrete images or fluorographic images) at a position of the patient 10 (lying on a patient table 14).

Alternatively, the computerized surgery assist computer 102 may receive anatomic image information of a patient 10 or a portion of a patient 10 obtained from a CT or MR scan.

For example, in such an embodiment, the anatomic image information may be a data set of three-dimensional imaging information. In an embodiment, the computerized surgery assist computer 102 may receive a data set of three-dimensional imaging information obtained while the patient 10 was in a neutral position. The anatomic image information may be received from an image processing computer server 18 positioned via wired or wireless data links 20, 22 between the x-ray scanner 16 (or, e.g., the CT or MR scanner) and the surgery assist computer 102. Optionally, the patient may have a three-dimensional positional sensor 100 affixed to the patient's body, and the surgery assist computer 102 may receive positional information via wired or wireless data link 110 from sensor 100. The surgery assist computer 102 may be programmed to display a visual representation of the anatomic image information on a computerized display 108; determine a target positioning value of a component from the anatomic image information, either automatically or with input from a surgeon; and may make additional measurements as desired or programmed (e.g., measurements of one or more anatomical landmarks and/or ratios of anatomical landmarks), either automatically or with input from a surgeon. The surgery assist computer 102 may further receive subsequent anatomic image information of the patient 10; display a visual representation of the subsequent anatomic image information on the display 108; and may make additional measurements or display additional markers, either automatically or with input from a surgeon.

The surgery assist computer 102 may have a receiver to receive information and data, including image data from the x-ray scanner 16 and/or CT or MR scanner; a processor or microcontroller, such as a CPU, to process the received information and data and to execute other software instructions; system memory to store the received information and data, software instructions, and the like; and a display 108 to display visual representations of received information and data as well as visual representations resulting from other executed system processes.

Figure 2C:
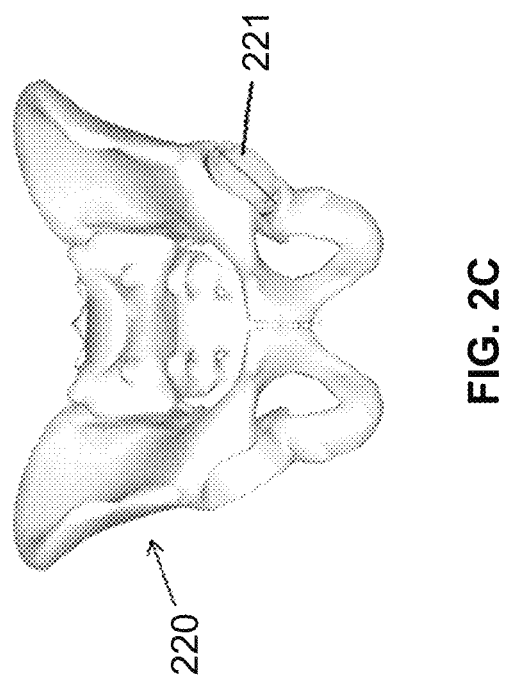
FIG. 2C shows a portion of a patient at a non-neutral position with backward tilt
Figure 2A:
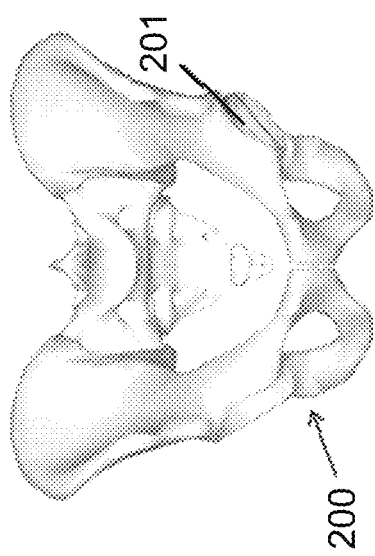
FIG. 2A shows a portion of a patient at a neutral position with no tilt.
Figure 2B:
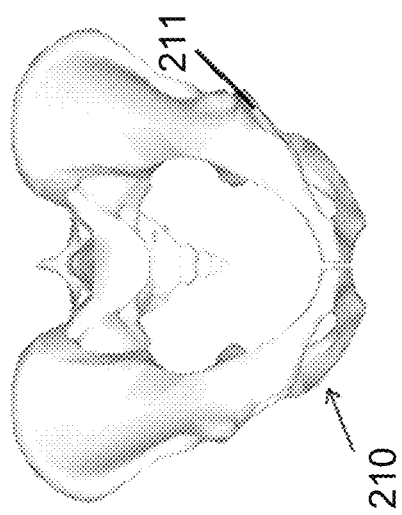
FIG. 2B shows a portion of a patient at a non-neutral position with forward tilt.

Such a system may allow a surgeon and/or other medical personnel to more accurately and consistently determine a proper placement of and position a component by helping a surgeon identify a target position for a component and making adjustments to the positioning value based on differences in initial anatomic image information and subsequent anatomic image information. Such differences may result, for example, when a patient and an imaging scanner are aligned differently with respect to each other when multiple sets of anatomic image information are acquired (e.g., pre-operatively at a neutral position of a patient and intra-operatively at a non-neutral position of the patient). FIGS. 2A-2C provide examples of a portion of a patient 200 (in this case the patient's pelvis) may appear differently when a patient is positioned in different orientations. For example, FIG. 2A shows a portion of the patient 200 in a neutral position with no tilt, while FIG. 2B shows a portion of the patient 210 with a forward tilt of about 20 degrees, and FIG. 2C shows a portion of the patient 220 having a backward tilt of about −20 degrees. Of course, moving a patient may also cause the portion of the patient to have different inclinations and anteversions, as a patient is generally manipulated in three-dimensional space. Importantly, small differences in a patient's orientation relative to a neutral position may provide different measurements of anatomical or component orientations, which could affect the outcome of a surgical procedure. For example, an acetabular cup 201 is positioned with an inclination of 40.0° and an anteversion of 20.0°. If pelvis 200 is tilted 20.0°, as pelvis 210 is in FIG. 2B, the acetabular cup 211 is measured to have an inclination of 37.3° and an anteversion of 4.3°. If pelvis 200 is tilted to −20.0°, as is pelvis 220 in FIG. 2C, the acetabular cup 221 is measured to have an inclination of 47.2° and an anteversion of 34.6°. Accordingly, when positioning a component in a patient during surgery, such as an acetabular cup during THA, a surgeon may need to account for the effects of the patient's orientation on positioning values such as tilt, inclination, and/or anteversion.

Figure 5:
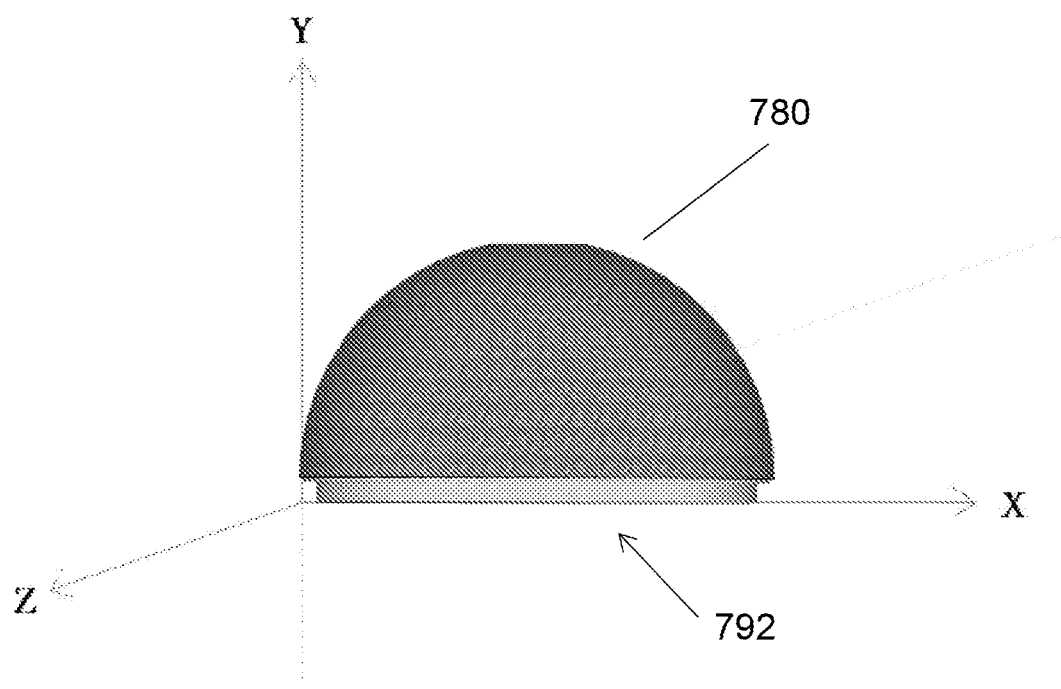
FIG. 5 shows a projected circle rotated along three axes that may be used to model an acetabular cup component in accordance with an embodiment of the present disclosure.

Adjustments to positional values of the acetabular cup, such as inclination, may be based on the study of a projected circle in three-dimensional space. The rotation of the circle in three-dimensional space may mimic the rotation of an acetabular cup. An acetabular cup may display shapes of ellipses under different angles of projection. Three rotational factors may affect the shape of the projected ellipse: Inclination (I)—rotation about the Z axis, Anteversion (A)—rotation about the Y axis, and Tilt (T)—rotation about the X axis. FIG. 5 illustrates an exemplary projection of a circle that may be used to model an opening 792 of an acetabular cup 780 with the X, Y, and Z axes labeled.

With reference to FIG. 5, the rotational matrices along the X, Y, and Z axes may be described as follows:

$$R_x(T) = \begin{bmatrix} 1 & 0 & 0 \\ 0 & \cos(T) & -\sin(T) \\ 0 & \sin(T) & \cos(T) \end{bmatrix}$$

$$R_y(A) = \begin{bmatrix} \cos(A) & 0 & \sin(A) \\ 0 & 1 & 0 \\ -\sin(A) & 0 & \cos(A) \end{bmatrix}$$

$$R_Z(I) = \begin{bmatrix} \cos(I) & -\sin(I) & 0 \\ \sin(I) & \cos(I) & 0 \\ 0 & 0 & 1 \end{bmatrix}$$

The following matrix may capture the initial circle lying on the X-Z plane:

$$\text{circle} = \begin{bmatrix} R*\sin(\theta) \\ 0 \\ R*\cos(\theta) \end{bmatrix}$$

The normal of the circle may be in the direction of the Y-axis and may be described as follows:

$$\text{Normal} = \begin{bmatrix} 0 \\ -1 \\ 0 \end{bmatrix}$$

After three rotations, the parametric equations of the circle projected on the X-Y plane may be described as follows:

$X = R*[\sin(\theta)*\cos(I)*\cos(A)+\cos(\theta)*\sin(A)]$; and $Y = R*\cos(T)*\sin(\theta)*\sin(I) - R*[-\sin(\theta)*\cos(I)*\sin(A)*\sin(T)+\cos(\theta)*\cos(A)*\sin(T)]$.

where X and Y represent the coordinates of the projected ellipse on the X-Y plane, R represents the size of the acetabular cup, and θ represents the parameter.

After three rotations along the three axes, the parametric equations of the normal of the circle surface may be described as follows:

$X_{normal} = \sin(I)*\cos(A)$ $Y_{normal} = -\cos(I)*\cos(T) + \sin(I)*\sin(A)*\sin(T)$ The normal of the circle has the property that it is always parallel to the minor diameter of the projected ellipse. Accordingly, the minor diameter of the projected ellipse may be derived and described as follows:

Minor Diameter = $\sin(a\ \cos(\sqrt{X_{normal}^2 + Y_{normal}^2}))*2*R$

The major diameter may be described as follows:

Major Diameter = $2*R$

Accordingly, the inclination value of the projected ellipse may be described as follows:

$$\text{Projected Ellipse } Incl. = \operatorname{atan}\left(\frac{X_{normal}}{Y_{normal}}\right)$$

Therefore, if an acetabular cup is placed or has target positioning values with a known inclination and anteversion, the inclination resulting after the acetabular cup is tilted (e.g., when the pelvis is tilted) may be calculated. Other positioning values may similarly be calculated, as will be apparent to one of ordinary skill in the art.

Unless otherwise expressly stated or obviously required by context, steps in methods described herein need not be performed in a particular order. Rather, an example order may be provided for ease of explanation.

Figure 3:
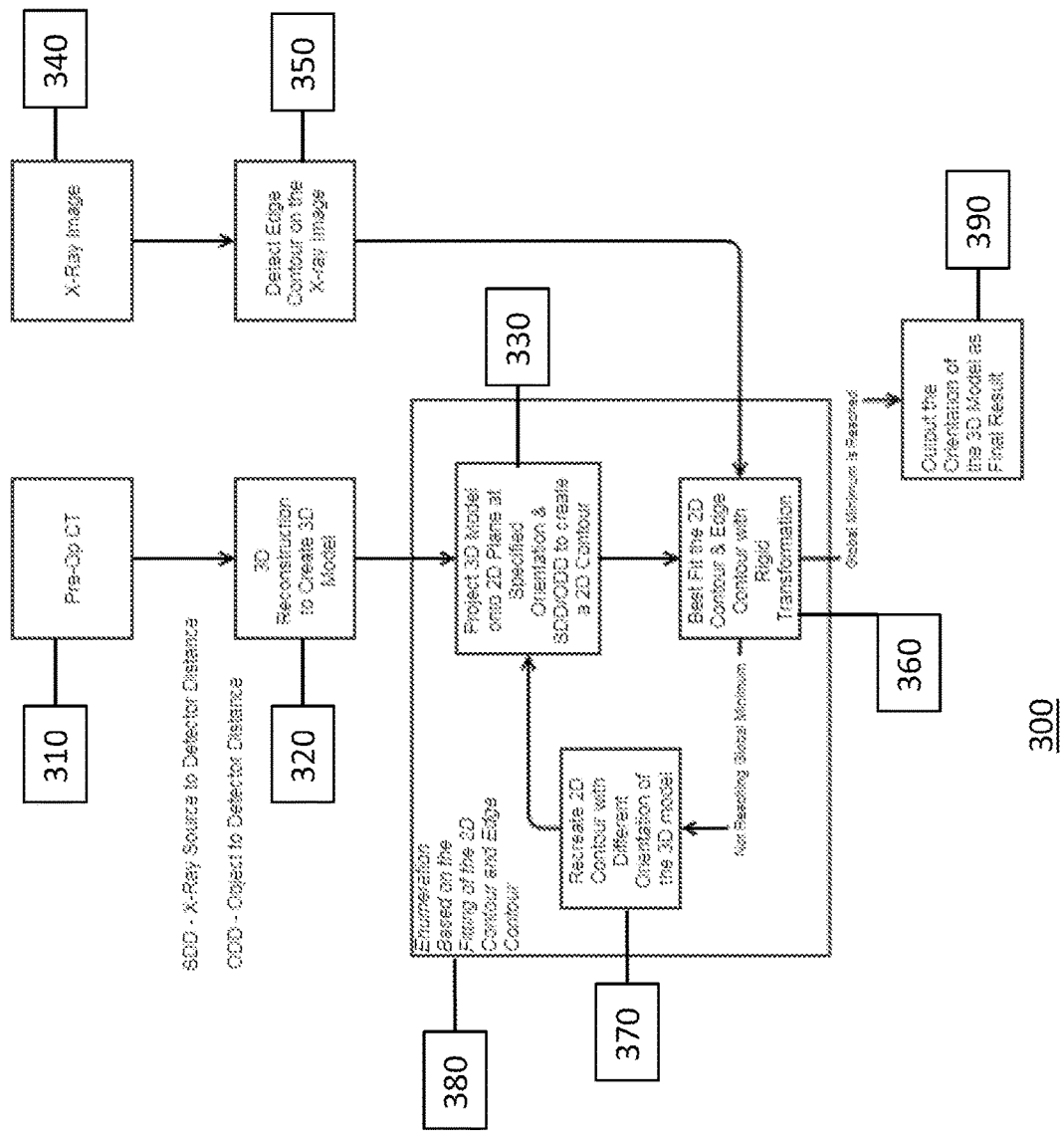
FIG. 3 is an exemplary flow chart diagram illustrating steps that may be taken to render one or more two-dimensional projections from a three-dimensional model of a portion of a patient in accordance with an embodiment of the present disclosure.

In an embodiment, the surgery assist computer 102 may be configured to implement one or more methods of the present disclosure. For example, with reference to FIG. 3, one method 300 may be used to position a component intra-operatively. The example method 300 may include a step 310 of receiving a data set of imaging information representing at least a first portion of a patient (e.g., a data set of three-dimensional imaging information from a CT or MR scan) in a neutral position. Method 300 may further include a step 320 of generating a three-dimensional model of the first portion of the patient based on the data set of imaging information. The three-dimensional model may be reconstructed based on a region grow algorithm, water shed algorithm, active contour algorithm, a combination of algorithms, or any algorithm that may be known to those of ordinary skill in the art for generating a three-dimensional model from a data set of imaging information.

Method 300 may additionally include a step 330 of iteratively rendering a plurality of two-dimensional projections from the three-dimensional model, each two-dimensional projection having a corresponding spatial orientation. The two-dimensional projections may be made at a specified orientation and distance (e.g., an x-ray-source-to-detector distance or an object-to-detector distance).

Alternatively, method 300 may include a step 330 of rendering a first two-dimensional projection from the three-dimensional model, the first two-dimensional projection having a corresponding spatial orientation, proceeding through step 360 (described in example form below), then repeating step 330 with a next sequential projection (or even an out of order projection).

Method 300 may include a step 340 of receiving intra-operative imaging information (e.g., an intra-operative x-ray image) representing the first portion of the patient. Method 300 may further include a step 350 of identifying a bony edge contour in the intra-operative imaging information. In an embodiment, the bony edge contour in the intra-operative imaging information may be detected using a canny edge detector algorithm, another edge-detection algorithm that may be known to those of ordinary skill in the art, a combination of algorithms, shape-based segmentation, or manual selection. In an embodiment, a canny edge detector process, such as in the exemplary process described above, may include the following steps: (1) apply a Gaussian filter to smooth the image in order to remove noise; (2) find the intensity gradients of the image; (3) apply non-maximum suppression to get rid of spurious responses to edge detection; (4) apply double threshold to determine potential edges; and (5) track by hysteresis to finalize the detection of edges by suppressing all the other edges that are weak and not connected to strong edges.

Method 300 may further include the step 360 of scoring each two-dimensional projection by calculating the distance of the bony edge contour in the intra-operative imaging information to a corresponding contour in each two-dimensional projection and identifying a global minimum score. Scoring step 360 may be performed using best-fit techniques. In an alternate embodiment, such as when the system initially renders only a first two-dimensional projection before proceeding through the method, step 360 may include scoring only the first two-dimensional projection, storing the score in memory, and repeating scoring step 360 for subsequent two-dimensional projections as they are rendered, then selecting a global minimum score from the plurality of scores. A repetitive process such as this may be illustrated by steps 330, 360, and 370 in FIG. 3. The process of repeating 330, 360, and 370 may be referred to as an enumeration process 380 based on the fitting of the two-dimensional projection and the detected bony edge contour from the intra-operative imaging information.

Method 300 may include a step 390 of outputting the orientation of the three-dimensional model as a final result. In an embodiment, step 390 may include outputting a transformation matrix for the two-dimensional projection having the global minimum score, the transformation matrix representing the orientation of the three-dimensional model relative to the neutral position when the two-dimensional projection having the global minimum score was rendered.

Figure 6:
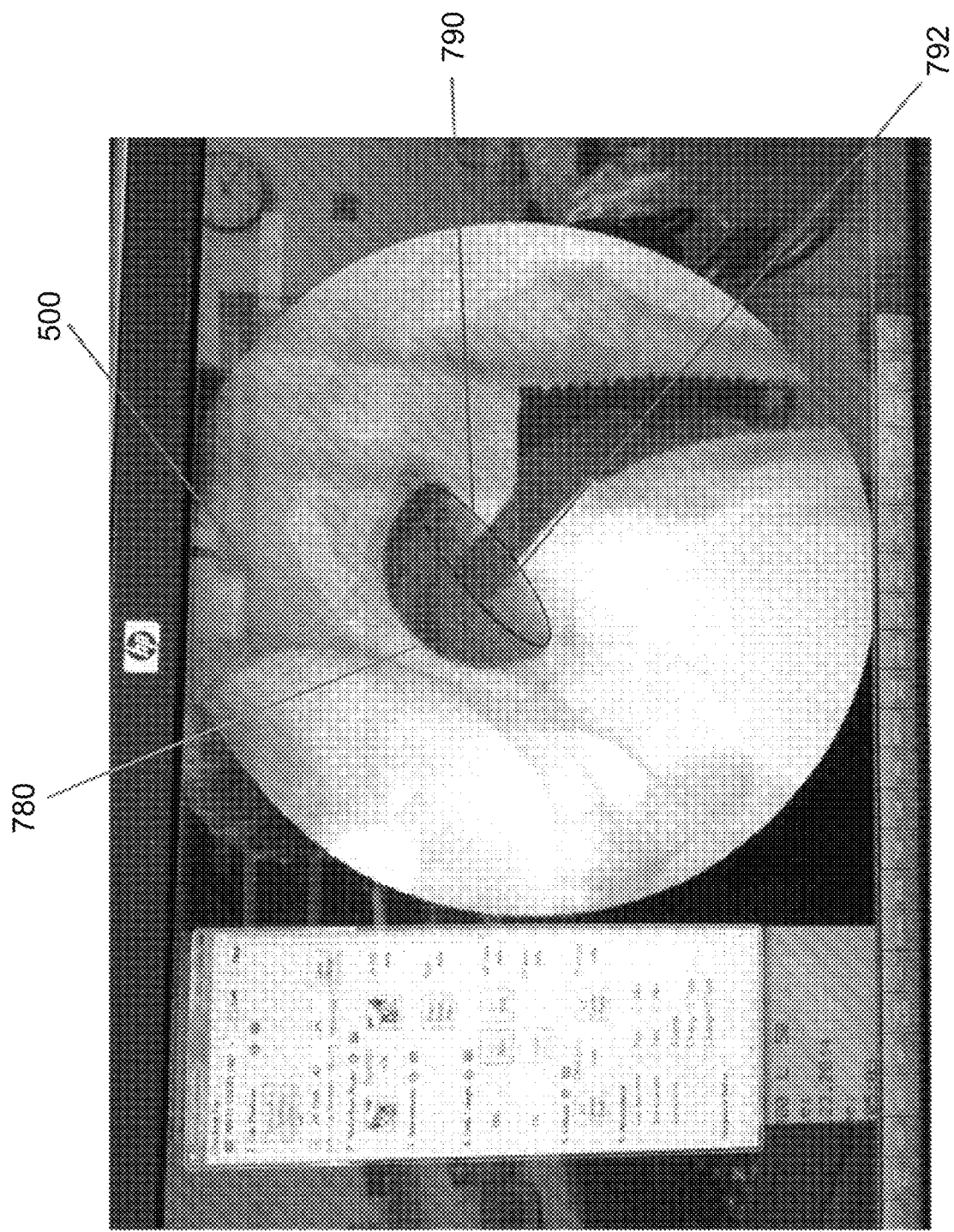
FIG. 6 shows a screen shot of a display including an intra-operative radiographic image including a superimposed ellipse representing a target placement of an acetabular cup component in accordance with an embodiment of the present disclosure'

In an embodiment, a method may include a step of calculating an adjustment factor based on the transformation matrix. The calculated adjustment factor may be used to output a visual indication of an intra-operative adjustment to be made to a component based on the adjustment factor to achieve a target component orientation. For example, FIG. 6 illustrates one embodiment of such a visual indication 790. Still referencing FIG. 6, for example, in a THA surgical procedure, an image of an ellipse 790 may be superimposed onto radiographic image 500 to illustrate how the opening of acetabular cup 792 should appear when properly aligned. In an alternate embodiment, a method may include the step of applying the calculated adjustment factor to an intra-operative leg length measurement and outputting a visual indication of an intra-operative adjustment to be made to the patient to achieve a target leg length measurement. In an embodiment, the radiographic image 500 (and any visual indication discussed in a similar context) may be displayed on display 108 from FIG. 1. In an embodiment, a visual indication may include an outline of the target component orientation; real-time inclination, anteversion, and tilt values of the component; target inclination, anteversion, and tilt values of the component; and/or combinations thereof.

Figure 4:
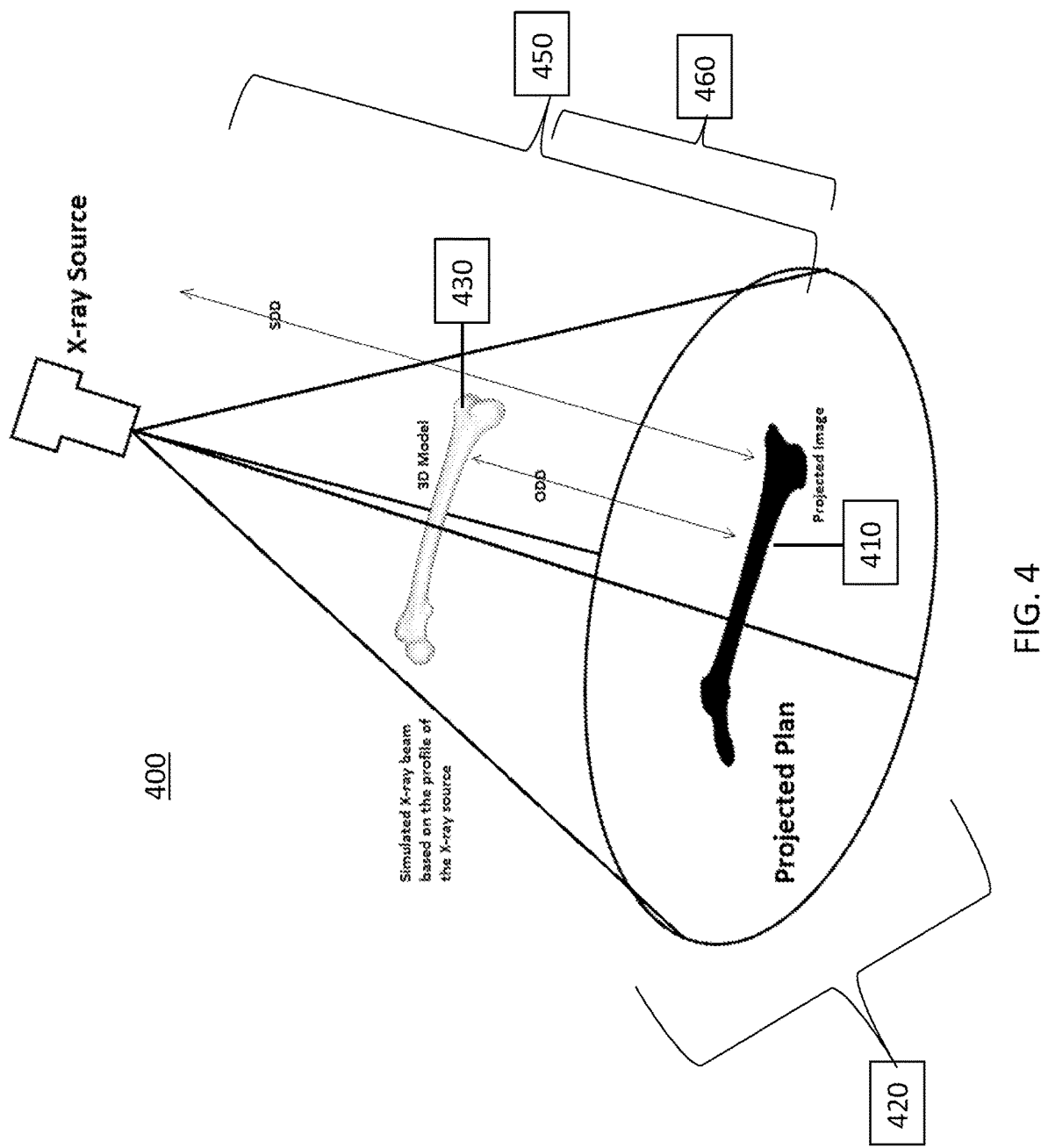
FIG. 4 is a diagram providing a conceptual model of a two-dimensional projection from a three-dimensional model in accordance with an embodiment of the present disclosure

FIG. 4 illustrates a conceptual model of a two-dimensional projection from a three-dimensional model 400 in accordance with an embodiment of the present disclosure. As discussed above, one or more two-dimensional projection(s) 410 may be rendered based on the three-dimensional model 430 onto a projected plan view 420. Projected plan view 420 may be comparable to an x-ray image, where the two-dimensional projection 410 may be comparable to an anatomical visualization on an x-ray image. Each two-dimensional projection may have a corresponding spatial orientation depending on the position of the x-ray source 16a to the three-dimensional model 430. Of course, FIG. 4 may represent a conceptualization of rendering two-dimensional projections, so there is not necessarily a physical x-ray source 16a or a physical three-dimensional model 430 (though it may be possible to visualize the three-dimensional model 430 on the display 108 in some embodiments). The two-dimensional projections may be rendered at a specified orientation and distance (e.g., an x-ray-source-to-detector distance 440 or an object-to-detector distance 450). The spatial relationship of the x-ray source 16a and the three-dimensional model 430 as well as distance(s) 450, 460 may want to be taken into account in certain embodiments to ensure accurate measurements.

In an embodiment, systems and methods of the present disclosure may be used to ensure consistent measurements between radiographic images taken of a patient at a neutral position and radiographic images taken of a patient in a non-neutral (e.g., intra-operative) position without having to ensure that the patient is precisely placed in a neutral position and, potentially, with less x-ray exposure, by simulating movement of the patient back to the neutral position using the three-dimensional model and calculating an adjustment factor taking into account the differences between the actual, non-neutral position of the patient and the patient in a neutral position.

Figure 7:
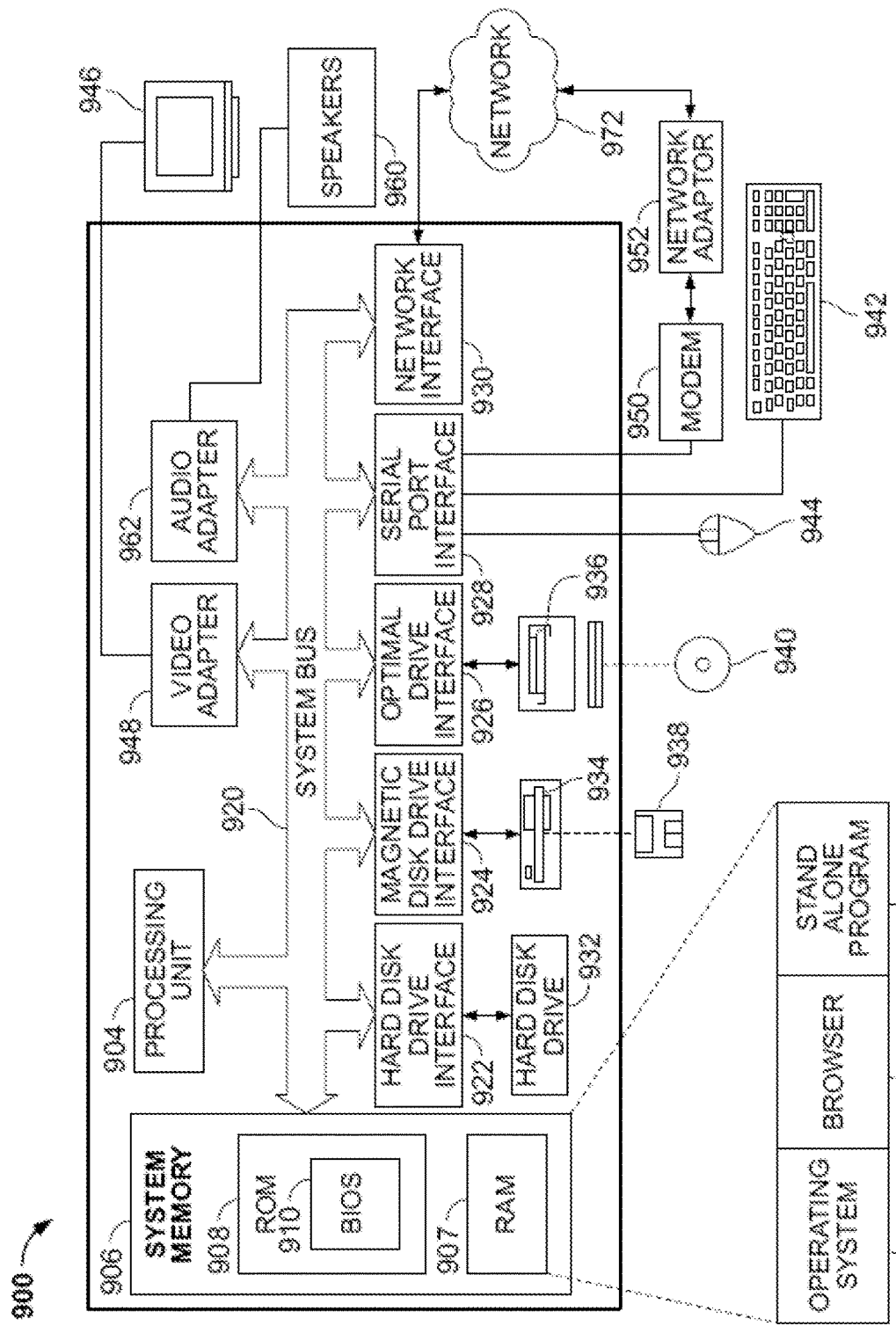
FIG. 7 shows an embodiment of a computer architecture according to the present disclosure.

FIG. 7 depicts exemplary hardware for a surgical method and workflow system for providing efficient acquisition and processing of radiographic images, generating and utilizing a three-dimensional patient model and determining a proper placement of a component during a surgery. The system, or part thereof, may take the form of a computer 900 that includes a processing unit 904, a system memory 906, and a system bus 920 that operatively couples various system components, including the system memory 906 to the processing unit 904. There may be only one or there may be more than one processing unit 904, such that the processor of computer 900 comprises a single central processing unit (CPU), or a plurality of processing units, commonly referred to as a parallel processing environment. The computer 900 may be a conventional computer, a distributed computer, a web server, a file server, a tablet or iPad, a smart phone, or any other type of computing device.

The system bus 920 may be any of several types of bus structures including a memory bus or memory controller, a peripheral bus, a switched fabric, point-to-point connections, and a local bus using any of a variety of bus architectures. The system memory 906 may also be referred to as simply the memory, and includes read only memory (ROM) 908 and random access memory (RAM) 907. A basic input/output system (BIOS) 910, containing the basic routines that help to transfer information between elements within the computer 900, such as during start-up, is stored in ROM 908. The computer 900 may further include a hard disk drive 932 for reading from and writing to a hard disk, not shown, a magnetic disk drive 934 for reading from or writing to a removable magnetic disk 938, and/or an optical disk drive 936 for reading from or writing to a removable optical disk 940 such as a CD-ROM or other optical media.

The hard disk drive 932, magnetic disk drive 934, and optical disk drive 936 may be connected to the system bus 920 by a hard disk drive interface 922, a magnetic disk drive interface 924, and an optical disk drive interface 926, respectively. The drives and their associated computer-readable media provide nonvolatile storage of computer-readable instructions; data structures, e.g., a catalog and a context-based index; program modules, e.g., a web service and an indexing robot; and other data for the computer 900. It should be appreciated by those skilled in the art that any type of computer-readable media that can store data that is accessible by a computer, for example, magnetic cassettes, flash memory cards, USB drives, digital video disks, RAM, and ROM, may be used in the exemplary operating environment.

A number of program modules may be stored on the hard disk 932, magnetic disk 934, optical disk 936, ROM 908, or RAM 907, including an operating system 912, browser 914, standalone program 916, etc. A user may enter commands and information into the personal computer 900 through input devices such as a keyboard 942 and a pointing device 944, for example, a mouse. Other input devices (not shown) may include, for example, a microphone, a joystick, a game pad, a tablet, a touch screen device, a satellite dish, a scanner, a facsimile machine, and a video camera. These and other input devices are often connected to the processing unit 904 through a serial port interface 928 that is coupled to the system bus 920, but may be connected by other interfaces, such as a parallel port, game port or a universal serial bus (USB).

A monitor 946 or other type of display device is also connected to the system bus 920 via an interface, such as a video adapter 948. In addition to the monitor 946, computers typically include other peripheral output devices, such as speakers 960 connected to the system bus 920 via an audio adapter 962, and printers. These and other output devices are often connected to the processing unit 904 through the serial port interface 928 that is coupled to the system bus 920, but may be connected by other interfaces, such as a parallel port, game port, or a universal serial bus (USB).

The computer 900 may operate in a networked environment using logical connections to one or more remote computers. These logical connections may be achieved by a communication device coupled to or integral with the computer 900; the application is not limited to a particular type of communications device. The remote computer may be another computer, a server, a router, a network personal computer, a client, a peer device, or other common network node, and typically includes many or all of the elements described above relative to the computer 900, although only a memory storage device has been illustrated in FIG. 9. The computer 900 can be logically connected to the Internet 972. The logical connection can include a local area network (LAN), wide area network (WAN), personal area network (PAN), campus area network (CAN), metropolitan area network (MAN), or global area network (GAN). Such networking environments are commonplace in office networks, enterprise-wide computer networks, intranets and the Internet, which are all types of networks.

When used in a LAN environment, the computer 900 may be connected to the local network through a network interface or adapter 930, which is one type of communications device. When used in a WAN environment, the computer 900 typically includes a modem 950, a network adapter 952, or any other type of communications device for establishing communications over the wide area network. The modem 950, which may be internal or external, is connected to the system bus 920 via the serial port interface 928. In a networked environment, program modules depicted relative to the personal computer 900, or portions thereof, may be stored in a remote memory storage device. It is appreciated that the network connections shown are exemplary and other means of, and communications devices for, establishing a communications link between the computers may be used.

The system can take the form of a computer program product 916 accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The medium can be an apparatus or device that utilizes or implements electronic, magnetic, optical, electromagnetic, infrared signal or other propagation medium, or semiconductor system. Examples of a computer-readable medium comprise a semiconductor or solid-state memory, magnetic tape, a removable computer diskette, a random access memory, a read-only memory, a rigid magnetic disk and an optical disk. Current examples of optical disks comprise compact disk-read only memory (CD-ROM), compact disk-read/write (CD-R/W) and DVD formats.

A data processing system suitable for storing and/or executing program code comprises at least one processor coupled directly or indirectly to memory elements through a system bus. The memory elements can include local memory employed during actual execution of the program code, bulk storage, and cache memory that provide temporary storage of at least some program code in order to reduce the number of times code is retrieved from bulk storage during execution.

Input/output or I/O devices (including, but not limited to, keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modems and Ethernet cards are just a few of the currently available types of network adapters.

Furthermore, computers and other related electronic devices can be remotely connected to either the LANs or the WAN via a digital communications device, modem and temporary telephone, or a wireless link. It will be appreciated that the Internet comprises a vast number of such interconnected networks, computers, and routers.

Figure 8:
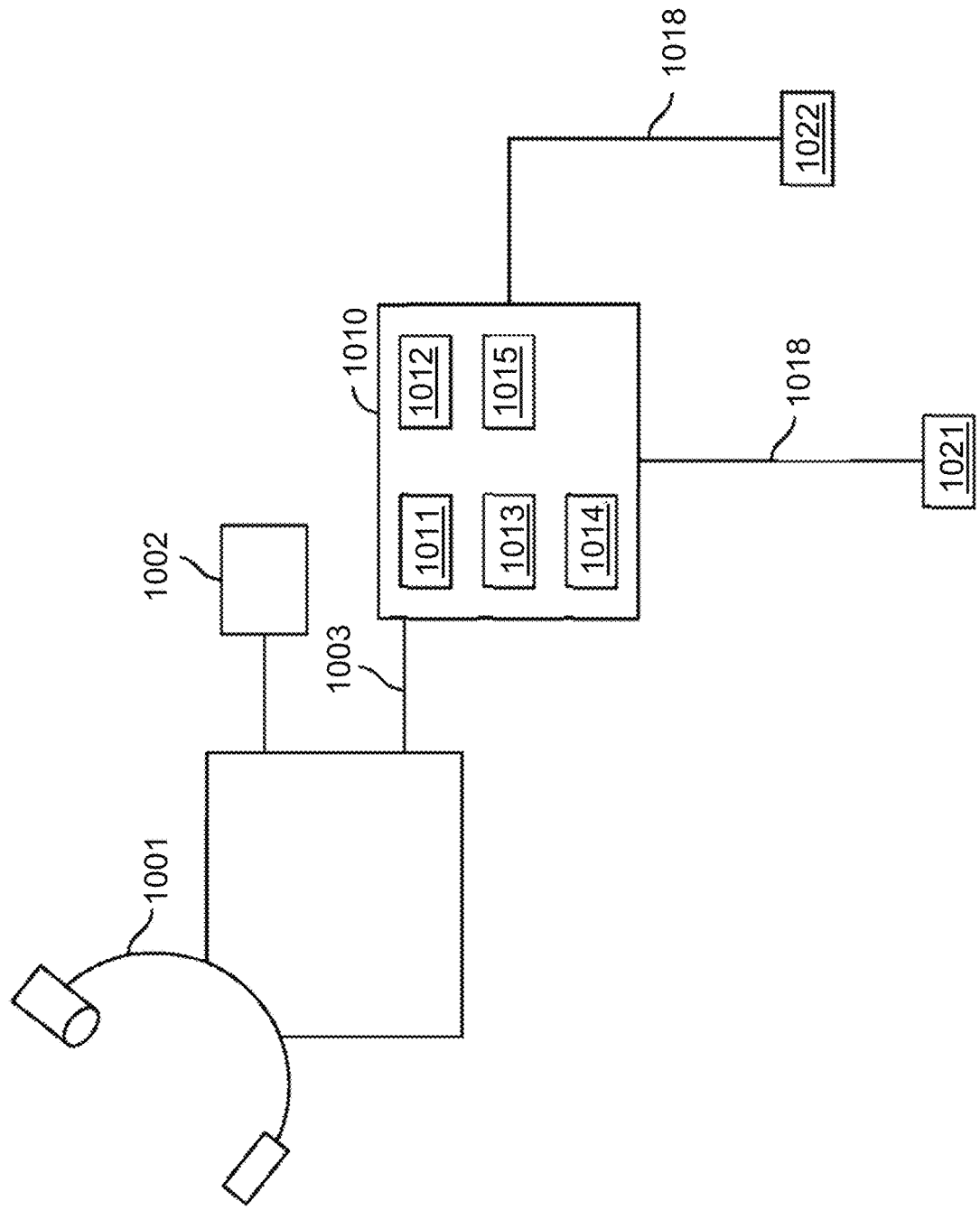
FIG. 8 depicts a block diagram of an exemplary environment that may be used to implement at least parts of the systems and methods of the present disclosure.

The methods and systems described in the present disclosure may be implemented, at least in part, using certain hardware. For example, referring to FIG. 8, a C-arm apparatus 1001 may capture video or image signals using x-rays. C-arm apparatus 1001 may, for example, capture an intraoperative x-ray image. The C-arm apparatus 1001 may have a display 1002 directly connected to the apparatus to instantly view the images or video. Display 1002 may be configured with a number of various inputs, including, for example, an input to receive one or more data sets of three-dimensional image information. A wireless kit 1010 may, alternatively or additionally, be attached to the C-arm apparatus 1001 via video port 1003 to receive the video or image signal from the C-arm apparatus 1001, the signal representing digital data of a radiographic image frame or plurality of frames. Video port 1003 may utilize a BNC connection, a VGA connection, a DVI-D connection, or an alternative connection known to those of skill in the art. Unique in the field in its ability to convert any wired image acquisition device (such as a C-arm) into a wireless imaging device, the wireless kit 1010 may be the Radlink Wireless C-Arm Kit. Wireless kit 1010 may include a resolution converter 1011 to convert the image signal to proper resolution for further transmission, frame grabber 1012 to produce a pixel-by-pixel digital copy of each image frame, central processing unit 1013, memory 1014, and dual-band wireless-N adapter 1015. The wireless kit 1010 may convert the received signal to one or more image files and can send the converted file(s), for example, by wireless connection 1018 to one or more computer(s) and operatively connected display(s) 1021, 1022.

The computer and operatively connected display may, for example, be a Radlink Galileo Positioning System ("GPS") 1021 or GPS Tablet 1022. The Wireless C-Arm Kit 1010 may receive, convert, and transmit the file(s) in real time. The methods described in the present disclosure may be implemented, for example, as software running on the GPS 1021 or GPS Tablet 1022 units. The GPS 1021 and GPS Tablet 1022 may also incorporate additional functions, such as those provided in the Radlink Pro Imaging with Surgeon's Checklist software.

The present invention also comprises a system and method for a surgical workflow. It allows radiographic images, such as X-ray images, to be acquired and displayed in digital form on a host computer for immediate review. Quality intraoperative X-ray images cannot be achieved with current technology. With the present system, however, high-quality digital radiographic images can be acquired quickly. The digital images can also be archived or forwarded to other medical personnel for further evaluation as required. With immediate acquisition of a high quality radiographic image, the surgeon is able to make the necessary adjustment on the patient or a prosthetic to perform the surgery in a more efficient manner.

Image Acquisition

Figure 9:
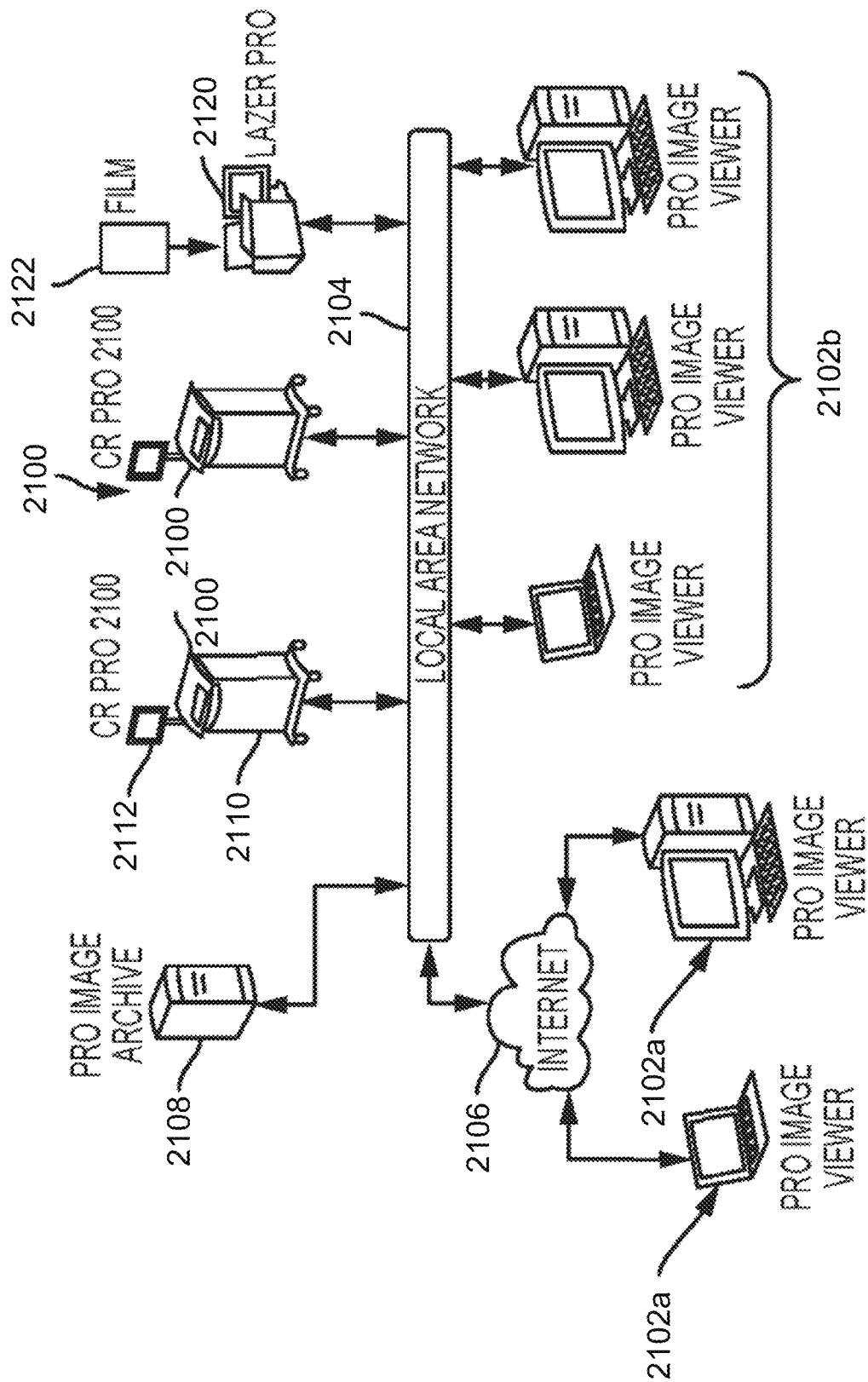
FIG. 9 shows an embodiment of the computer architecture of the present invention.
Figure 10:
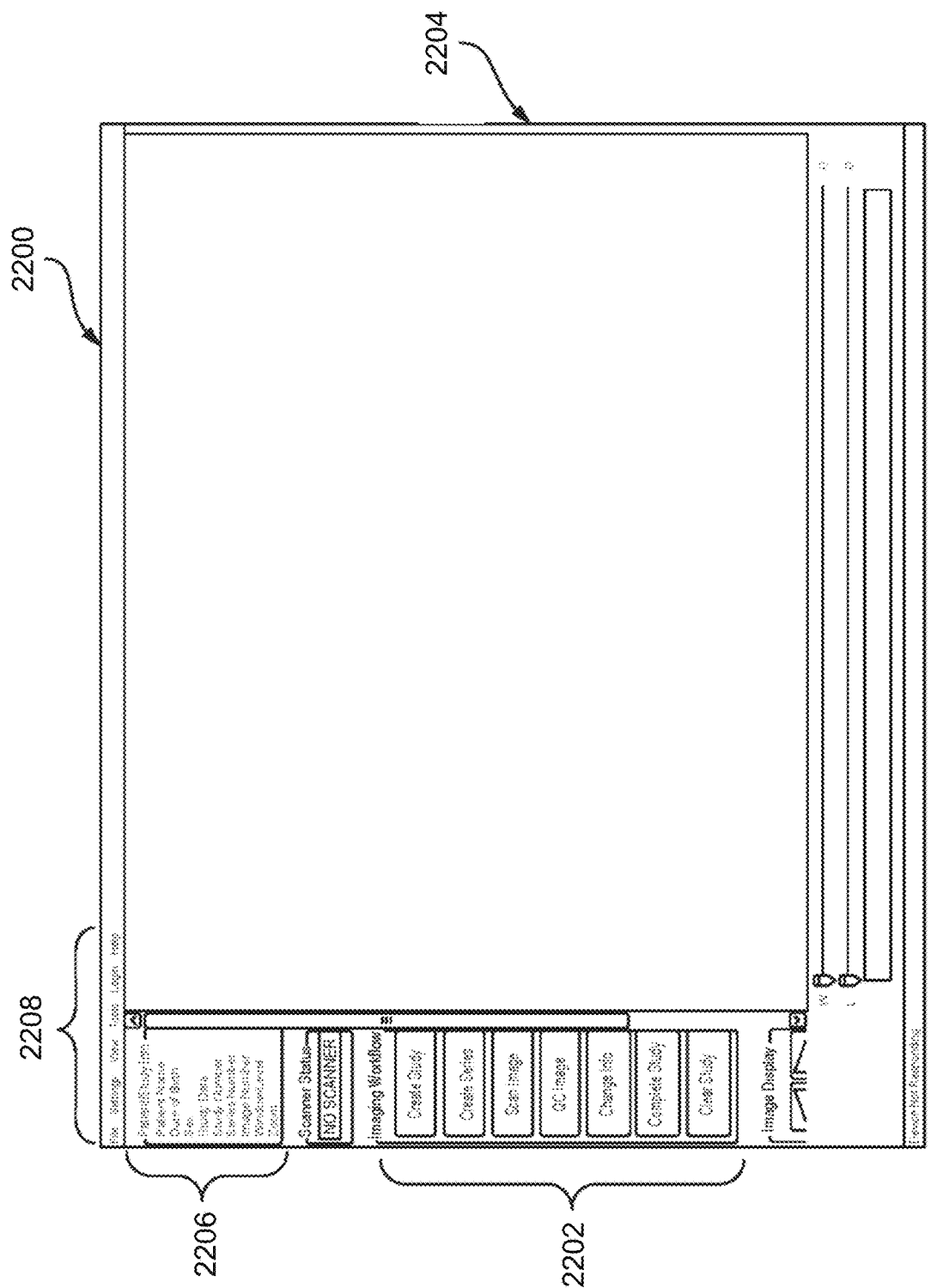
FIG. 10 shows an embodiment of an image frame.

Digital radiographic images can be acquired via digital radiography or computed radiography. For example, as shown in FIG. 9, in computed radiography, a radiological device 2100 scans erasable phosphor plates exposed to X-rays and transmits the images to an imaging onboard computer 2110 (either through a wired or wireless connection) for review, archiving, or forwarding to other facilities 2102a, 2102b through a local area network 2104 and/or through the Internet 2106 for further evaluation and/or archiving 2108. In some embodiments, a scanner 2120 may scan existing X-ray files 2122 and convert them to digital radiographic images. Acquired images can be saved in a variety of formats, such as tiff, jpeg, png, bmp, dicom, and raw formatted images for both reading and writing.

Digital radiography offers numerous advantages over traditional X-ray methods. For example, digital radiography generates low radiation levels, specifically, below levels required by traditional X-ray machines to capture a detailed image on radiographic film 2122. In addition, a radiographic image 2500 can be viewed much quicker than with traditional X-ray film due to the reduced image acquisition time. Therefore, overall exposure to radiation is reduced due to the lower levels and shorter exposure times.

As shown in FIGS. 9-16, once a digital radiographic image 2500 has been acquired, the radiographic image 2500 can be processed and optimized by a computer 2110, or any other computing device, such as a tablet, a smart phone, and the like. The computer 110 will display on a display device 2112 (such as a monitor, television, screen, tablet, etc.) a main screen or main window 2200 providing workflow action buttons 2202, an image frame 2204 to display the radiographic image 2500, an information frame 2206 displaying the information associated with the radiographic image displayed, and typical menu items 2208.

Figure 11:
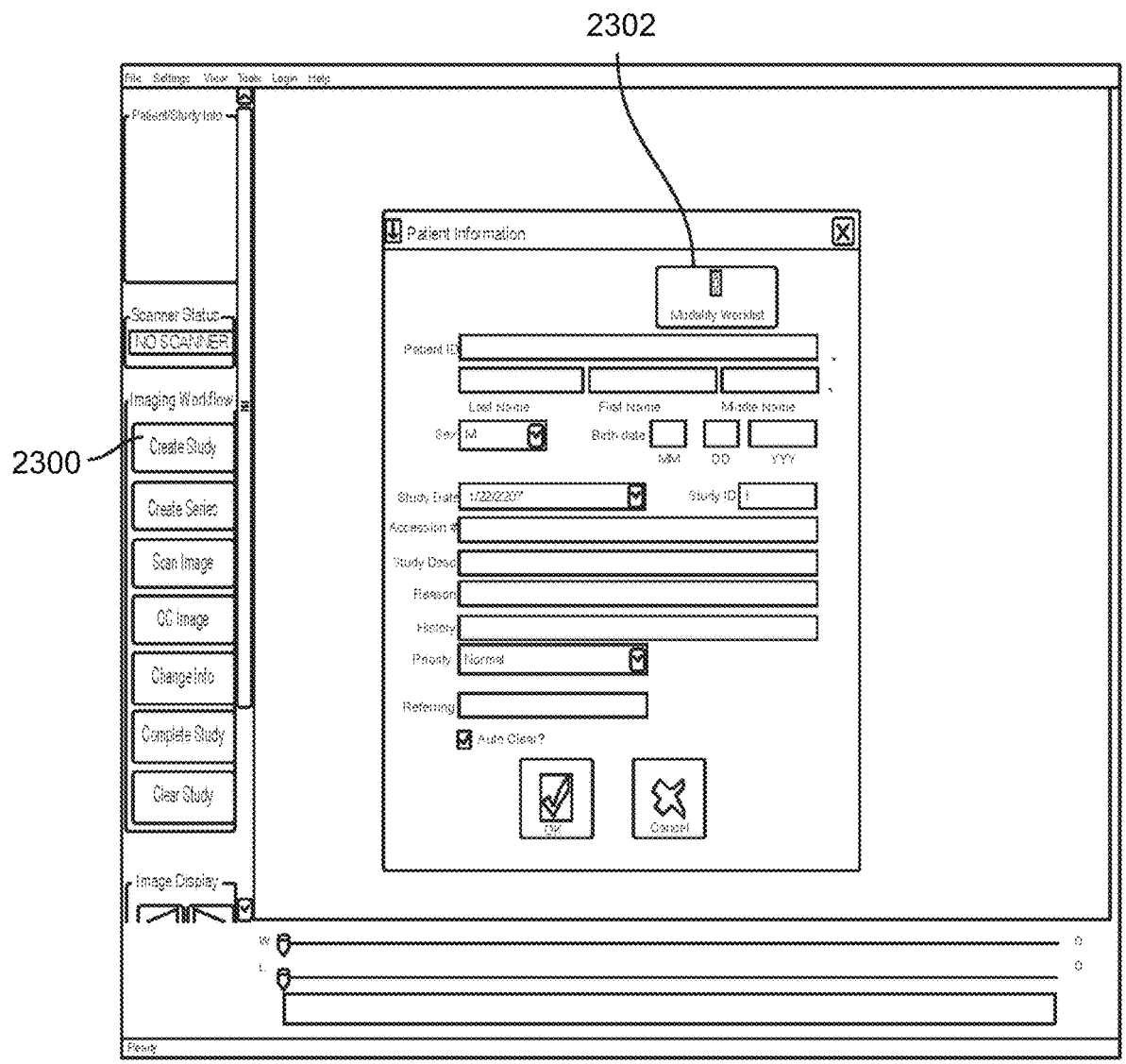
FIG. 11 shows an embodiment of a patient information window.

The workflow 2202 steps may comprise creating a study, creating a series, scanning an image, performing quality control on the image, changing information, completing the study, and clearing the study. Creating a study begins with entering information related to the patient, the patient's medical condition, a recommended medical procedure, and any other information relevant to the patient and the condition being treated or diagnosed. As shown in FIG. 11, a create study button 2300 can be provided to begin this process. A patient information window 2302 may be provided with various fillable fields to input the relevant information. Once a study is created, an acquired radiographic image 2500 can be uploaded and saved to that study.

Figure 12:
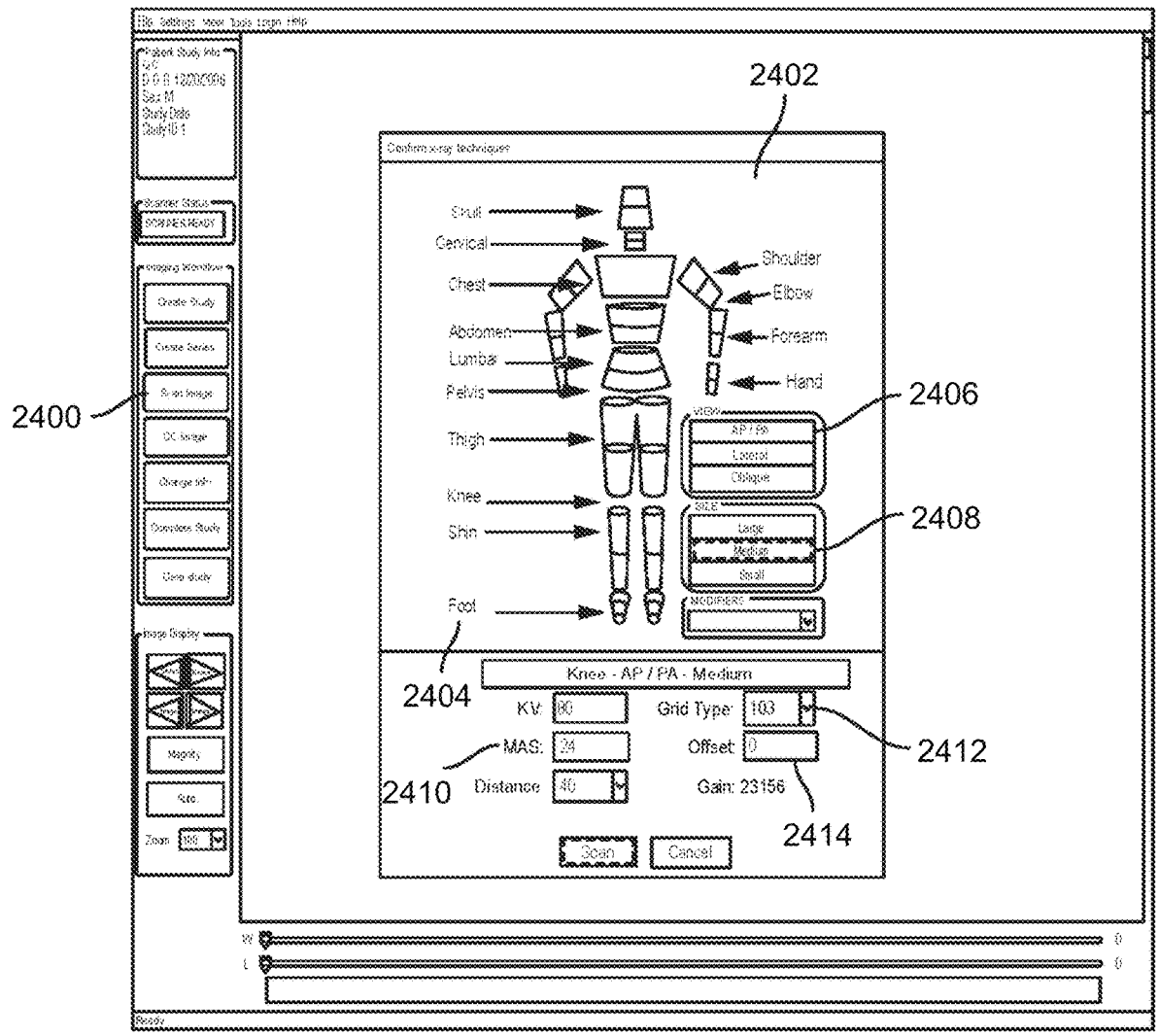
FIG. 12 shows an embodiment of a scanning window.
Figure 13:
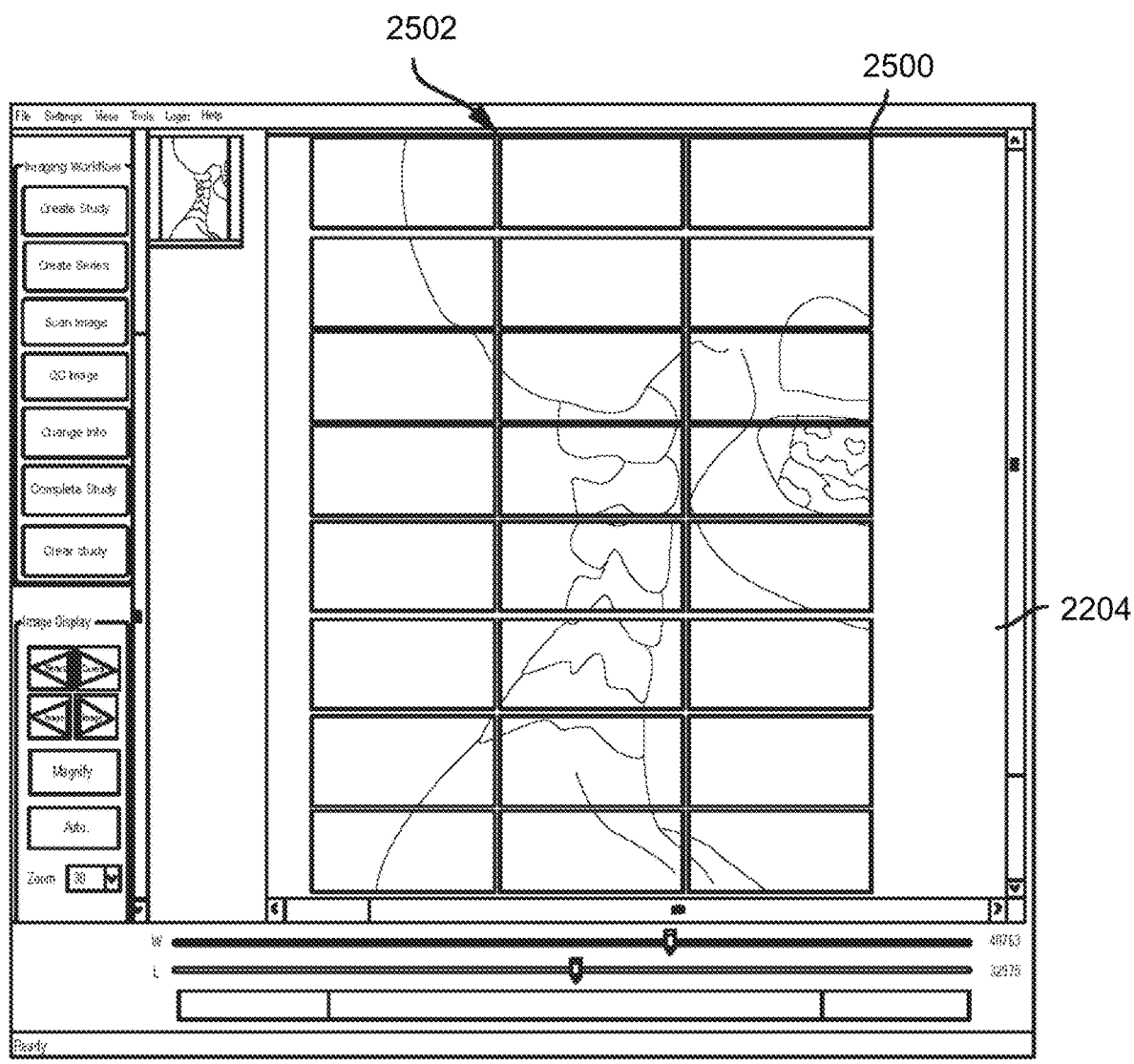
FIG. 13 shows an embodiment of a digital radiographic image being acquired.

Scanning an image allows the user to acquire a radiographic image of a particular body part for processing. As shown in FIG. 12, a scan image button 2400 may be provided, actuation of which opens a scanning window 2402 that allows the user to select such configurations as a particular body part or region 2404 to be scanned, the view of the scan 2406, the patient's size 2408, the particular technique used 2410, the grid type 2412, the offset 2414, and the like. Selecting a body part may involve selecting the corresponding body part of an image displayed on the image frame, or selecting the body part from a list of body parts. Once the scan is initiated, the images may be displayed line by line in the image frame 2204 as it is being scanned as shown in FIG. 13. In some embodiments, a grid 2502 may be provided. Using the grid 2502, the image orientation can be verified and adjusted. For example, the image 2500 can be rotated by any degree, then flipped, inverted, or otherwise adjusted, and processed further as discussed below.

Figure 14:
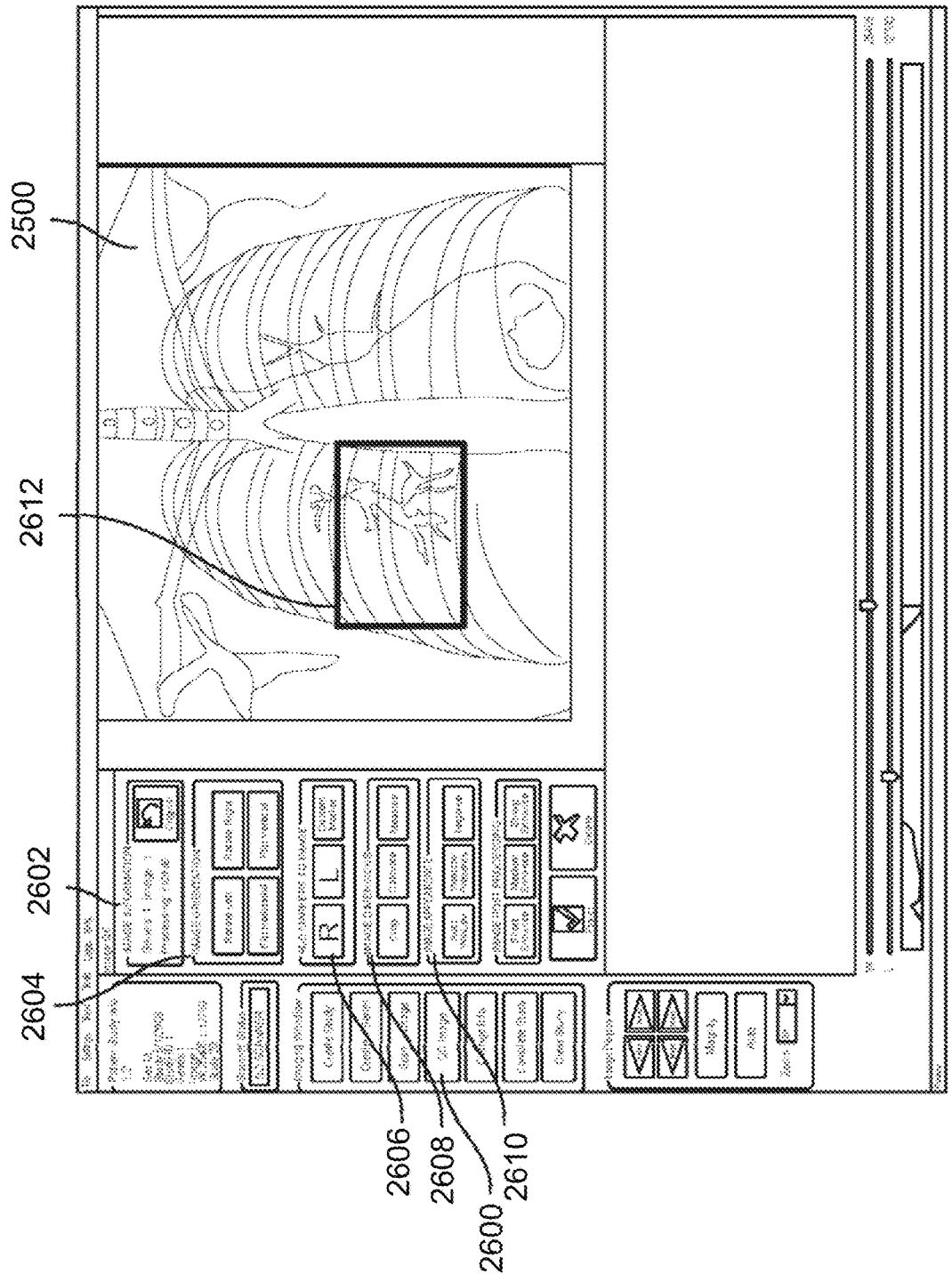
FIG. 14 shows an embodiment of an image quality check window.
Figure 15:
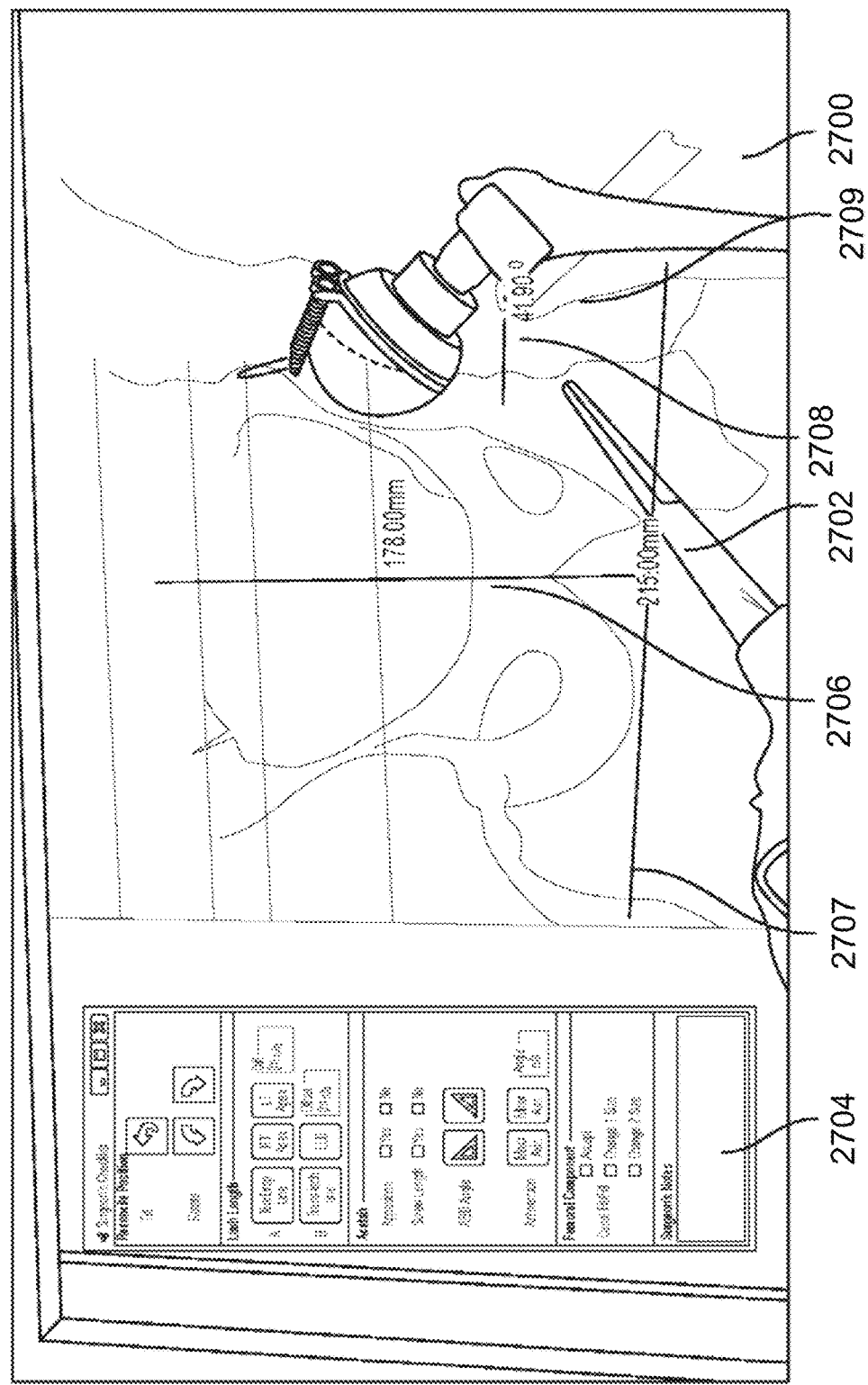
FIG. 15 shows an embodiment of an image displayed on a touchscreen for processing.

Once the image 2500 has been acquired, the user can perform a quality control (QC) check on the image. As shown in FIG. 14, a layout template or a QC image button 2600 may be provided, actuation of which opens an image QC window 2602 providing a number of features to improve the quality and layout of the radiographic image 2500 acquired. For example, the image QC window 2602 may provide features to orient the image 2604, add markers 2606 to the image, annotate the image, change the image dimensions and take measurements or sizing on the image 2608, change the appearance of the image 2610, and the like.

Therefore, using the image QC window 2602, the user can process, modify, and interact with the image 2500, such as rotating to the left, rotating to the right, flipping horizontally, flipping vertically, cropping, zooming, magnifying, moving or panning the image, changing the window width, inverting the image to a negative image, adjusting the level (brightness and contrast) of the image, adding or creating markers to indicate various information about the image, adding measuring lines to determine lengths, distances, angles, and the like. Additional features can be added, and any feature can be removed and added back again so as to configure the layout template according to the user's needs.

In some embodiments, processing, modifying, and interacting with the image 2500 can be done on the image frame 2204 instead of with the image QC window 2602. For example, the display device 2110 showing the radiographic image 2500 may be a touchscreen device 2700 as shown in FIG. 13. The user may use his fingers or a pointing device or any tool 2702 to make gestures on a touchscreen 2700 to effectuate the desired feature and view parameters that would assist the surgeon during the surgical procedure. For example, if a scanned image 2500 is not properly aligned in the image frame 204, the user may tap or double tap the touchscreen 2700 on the scanned image 2500 and cause it to automatically rotate into the proper orientation. Gridlines 2502 may be displayed on the image frame 2204 as a guide for proper alignment. Alternatively, the user can place one or more fingers on the image frame 2204 and make a rotating gesture to cause image 2500 to rotate in the direction of the gesture. In some embodiments, the user may input specific values as the precise measurement for modification. For example, the user may indicate that the radiographic image 2500 is to be rotated by a specified angle of rotation.

Taking measurements can be done in a similar fashion. Actuation of any of the features in the image QC window 2602 may open a tools window 2704 containing a checklist with electronic tools that are specific for the feature actuated. For example, if a measurement button is actuated, a tools window 2704 may be displayed with a set of electronic tools that can be actuated to take measurements on the radiographic image. Actuating a length tool may allow the user to draw lines 2706 on the radiographic image 2500 which represents a length on the image 2500. Actuating an angle tool allows the user to draw angles 2708 and adjust the angle 2708 drawn so that the user can measure the angle between structures shown on the radiographic image 2500. Using the touchscreen 2700, the user is able to move the lines 2706 or angles 2708 to various positions on the radiographic image 2500 to take the measurement of various structures on the radiographic image. Lines 2706 and angles 2708 already drawn can be modified to change the length and/or angles. New lines and angles can also be created to measure multiple structures.

Based on measurements determined on the radiographic image 2500, the surgeon or other medical personnel can make adjustments during the surgical procedure, such as adjusting the position of the patient, the patient's body part, a prosthetic, a surgical tool, and the like to achieve a desired position, thereby eliminating any delay and interruption during the surgical procedure.

By way of example only, as shown in FIG. 13, a radiographic image of the hip area is displayed on a touchscreen 2706 along with the surgeon's checklist 2704 to allow the surgeon to check desired parameters to assure the surgical procedure will be performed efficiently and accurately. Based on the acquired image, the surgeon can make sure the left and right sides of the image are properly displayed and the contrast adjusted. The surgeon may touch a point on the mid sacrum. This displays a vertical line 2706 which can be used to determine the presence of pelvic tilt. Significant tilt or rotation of the pelvis would render subsequent measurements inaccurate. If this line 2706, starting at mid sacrum passes to one side of the symphysis pubis by more than, for example, a centimeter, then the patient's position should be adjusted so that the line 2706 is as close to mid symphysis as possible to reconcile pelvic tilt.

Next, the surgeon may actuate a horizontal line tool to draw either a trans-ischial or trans-ischial tuberosity line 2707 to reconcile pelvic rotation. This identifies a horizontal axis orientation in relation to the pelvis. This line 2707 creates, for example, a reference for subsequent angular and linear limb length and offset measurements.

The surgeon may then actuate an angle tool from the checklist 2704 to display an acetabular abduction angle 2708, for example, at 45 degrees. This 45 degree angle is referenced to the previously drawn horizontal (teardrop or trans-ischial) line 2707 representing the transverse pelvic axis.

The surgeon may actuate a measure offset tool from the checklist 704 to display a measuring line 2709. In this example, the measuring line 2709 is displayed as a line parallel to horizontal 2707. The measuring line 2709 can be set to start at any predetermined length, for example, the measured amount on the pre-op X-ray. This is, generally speaking, the amount of lateralization of the femur in relation to the pelvis, which is as important as limb length in THA.

With the measuring line 2709, major and minor diameters of acetabular component can be determined. These numbers feed into a calculation of "acetabular anteversion," another important parameter in THA.

Actuation of an annotation tool permits annotation of accuracy of femoral component sizing. All annotations can be saved as part of the patient's medical record. Once the combination of these steps are complete, the surgeon is in a much better position to accurately place the acetabular component and assure that the location of the screws is acceptable. By performing this combination of steps from the checklist and getting immediate results during the actual surgical procedure, the surgeon is able to perform the surgery more accurately and quicker than without the checklist. Other parameters to be checked may be determined by the surgeon as needed.

Specific regions of interest can also be isolated and that region of interest modified in the ways described above. For example, the user can click on the image 2500 and create a box 2612 around the region of interest to display a blow-up of the region of interest.

Figure 16:
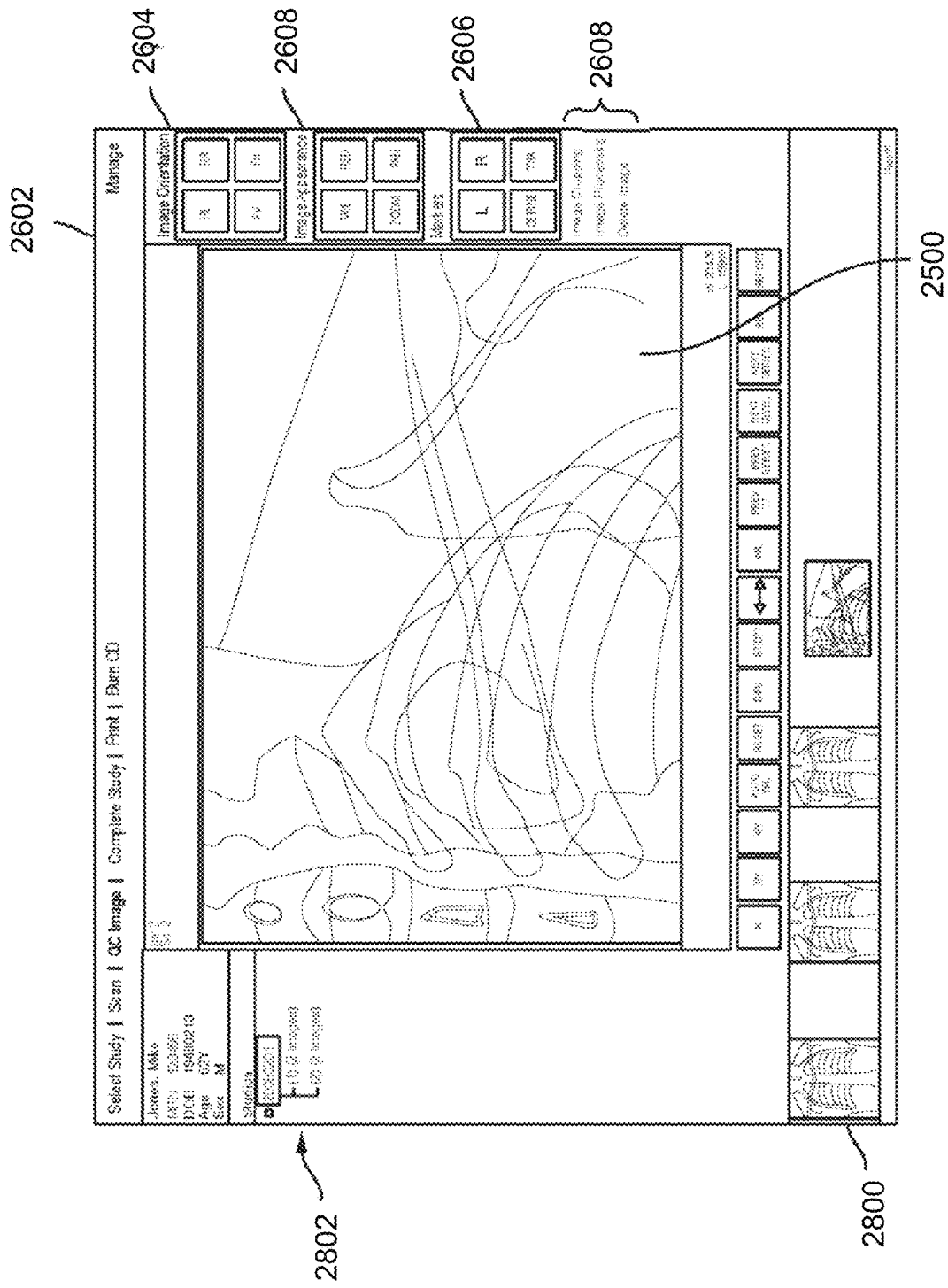
FIG. 16 shows another embodiment of an image frame of a series of a study.

Multiple images may be acquired and saved as a series of a study. Selected images can be displayed together or individually in the image frame 2204. All images in the series may be provided as thumbnail images 2800 adjacent to the image frame 2204 to show all images related to the image 2500 displayed in the image frame 2204 as shown in FIG. 16.

Once the image 2500 has been acquired, before, during, or after any processing, the system can provide a checklist of parameters for the user to review and indicate whether the necessary steps have been performed. The checklist can include, but is not limited to, the following items or parameters: orientation of the radiographic image, component orientation, cup apposition (in-growth), cup anteversion angle, cup abduction angle, screw positions, femoral sizing, femoral component alignment, limb length, and offset between the first edge of a bone and a second edge of the bone.

Additional buttons may be provided to delete the image, save the image, clear the image, undo an action, redo an action, and the like. Each of these steps can be done during the operation without the surgeon having to leave his patient.

Saved files can be opened in the typical manner from a database or directory 2802. The system may display a worklist window for the user to view and select study from a worklist. The worklist may be organized by a specific filter, such as name, date, medical condition, and the like. Selection of a specific filter displays all studies categorized under that filter. Each study may have additional information associated with it. The list of studies may be sortable based on any of the additional information. Selection of a study displays an image window that allows the surgeon to review acquired digital radiographic images.

Any created study can be transmitted to another computer 2102a, 2102b via a local area network 2104 and/or the Internet 2106, saved to a hard drive or saved to any other type of non-transitory computer readable medium, such as a CD, DVD, USB drive, and the like.

Additional workflow states include the state of arrival of a study, a verification state to indicate that a study is complete and accurate, a dictated state to indicate a report for a study has been dictated, a transcribed state to indicate that a report has been transcribed, and a finalized state to indicate that a report has been approved and finalized.

This system allows the user to take an X-ray before and during the middle of an operation and make the necessary adjustments immediately upon acquiring the results to greatly improve the accuracy of the surgical procedure. In addition, the accuracy resulting from each step synergistically improves the accuracy of any subsequent step and, therefore, significantly improves the outcome of the total surgical procedure in a way that cannot be achieved by improving the accuracy of any one step alone.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

What is claimed is:

1. A method of positioning a component intra-operatively comprising the steps of:

providing a computerized surgical workflow program to a computer device, the surgical workflow program guiding a user through steps of a surgical procedure;

iteratively registering a plurality of two-dimensional projections of a portion of a patient from a three-dimensional model of the portion of the patient, the three-dimensional model being generated from a data set of imaging information obtained at a neutral position, and each two-dimensional projection having a spatial orientation;

receiving through the computer device, from the user, as part of a surgical workflow offered by the surgical workflow program, activation of a graphical tool for performing intraoperative measurements;

receiving an intraoperative radiographic image data pertaining to a patient and pertaining to a first surgical placement of a prosthetic implant during a surgery;

displaying a visual representation of the intraoperative radiographic image data on an electronic display of the computer device;

providing a graphical interface to the user on the electronic display that allows the user to mark an anatomical structure on the visual representation of the radiographic image data on the electronic display;

upon receipt of the user's marking the anatomical structure on the visual representation of the radiographic image data, superimposing at least one of (a) a measuring line and (b) a measuring angle onto the displayed visual representation of the radiographic image data on the electronic display, wherein, in response to the anatomical structure marked, the measuring line or the measuring angle are automatically drawn by the surgical workflow program with a specific set of parameters;

scoring each two-dimensional projection against an intra-operative image by determining a best fit of each projection to the intra-operative image and calculating a spatial difference between corresponding points;

identifying a global minimum score reflecting the smallest spatial difference between the corresponding points on the two-dimensional projection and the intra-operative image and selecting the two-dimensional projection having the global minimum score as an intra-operative projection;

obtaining values representing the orientation of the three-dimensional model corresponding to the intra-operative projection;

calculating an adjustment factor based on the difference in the values representing the orientation of the three-dimensional model at the intra-operative projection position and values representing the orientation of the three-dimensional model at the neutral position;

displaying to the user on the electronic display measurement information associated with the at least one of (a) the measuring line and (b) the measuring angle onto the displayed visual representation of the radiographic image data; and repeating the steps of receiving intraoperative radiographic image data pertaining to the patient and pertaining to a subsequent surgical placement of the prosthetic implant during the surgery, displaying visual representations of the intraoperative radiographic image data on the electronic display of the computer device, and providing the graphical interface to the user on the electronic display to mark the visual representation of the radiographic image data on the electronic display until a desired placement of the prosthetic implant is achieved.

2. The method of claim 1, wherein the electronic display is a touchscreen display and receipt of the user's marking the visual representation of the radiographic image data is through the touchscreen display, and further comprising, modifying at least one of (a) the measuring line and (b) the measuring angle upon receipt of a manipulation of the touchscreen display by the user; and displaying to the user on the electronic display measurement information associated with at least one of the modified measuring line and the modified superimposed measuring angle.

3. The method of claim 2, further comprising steps of:

moving at least one of (a) the measuring line and (b) the measuring angle upon receipt of a manipulation of the touchscreen display by the user; and displaying to the user on the electronic display measurement information associated with the movement of the at least one of (a) the measuring line and (b) the measuring angle.

4. The method of claim 2, further comprising a step of reorienting the visual representation of the radiographic image data on the electronic display upon receipt of a manipulation of the touchscreen display by the user.

5. The method of claim 1, further comprising the step of outputting a visual indication of an intra-operative adjustment to be made to a component based on the adjustment factor to achieve a target component orientation.

6. The method of claim 1, further comprising the step of applying the adjustment factor to an intra-operative leg length measurement and outputting a visual indication of an intra-operative adjustment to be made to the patient to achieve a target leg length measurement.

7. The method of claim 1, wherein the step of scoring a first two-dimensional projection occurs before or during the step of registering a subsequent two-dimensional projection.

8. The method of claim 1, wherein each of the plurality of two-dimensional projections is registered before scoring any two-dimensional projection.

9. The method of claim 1, further comprising identifying a reference point on the intra-operative image using one of a canny edge detector algorithm, a shape-based segmentation algorithm, manual selection, and a combination thereof.

10. The method of claim 1, wherein the three-dimensional model of the portion of the patient is generated by applying one of a region grow algorithm, a water shed algorithm, an active contour algorithm, and a combination thereof to the data set of imaging information.

11. The method of claim 1, wherein:
upon receipt of the user marking the anatomical structure on the visual representation of the radiographic image data, the superimposing step superimposes the measuring line onto the displayed visual representation of the radiographic image data on the electronic display; and
the displayed measurement information comprises length information associated with a length of the measuring line with respect to the displayed visual representation of the radiographic image data.

12. The method of claim 1, wherein:
upon receipt of the user marking the visual representation of the radiographic image data, the superimposing step superimposes the measuring line onto the displayed visual representation of the radiographic image data on the electronic display; and
the displayed measurement information comprises angle information associated with an angle of the measuring line with respect to the displayed visual representation of the radiographic image data.

13. A method for positioning a component intra-operatively comprising the steps of:
receiving a data set of imaging information representing at least a first portion of a patient in a neutral position;
generating a three-dimensional model of the first portion of the patient based on the data set of imaging information;
receiving intra-operative imaging information representing the first portion of the patient;
identifying a bony edge contour in the intra-operative imaging information;
iteratively rendering a plurality of two-dimensional projections from the three-dimensional model, each two-dimensional projection having a corresponding spatial orientation;
scoring each two-dimensional projection by calculating the distance of the bony edge contour in the intra-operative imaging information to a corresponding contour in each two-dimensional projection;
identifying a global minimum score;
outputting a transformation matrix for the two-dimensional projection having the global minimum score, the transformation matrix representing the orientation of the three-dimensional model relative to the neutral position when the two-dimensional projection having the global minimum score was rendered;
calculating an adjustment factor based on the transformation matrix;
receiving intraoperative radiographic image data pertaining to a hip area of a patient and pertaining to a first surgical placement of a prosthetic hip implant during a surgery on a computerized device having a touchscreen display;
displaying a visual representation of the intraoperative radiographic image data on the touchscreen display of the computerized device;
upon receipt of a user touching a point corresponding to a mid sacrum of the hip area of the patient on the visual representation of the intraoperative radiographic image data on the touch-screen display superimposing a first measuring line onto the displayed visual representation of the intraoperative radiographic image data on the touchscreen display of the computerized device, wherein the measuring line starts at a location on the visual representation of the intraoperative radiographic image data associated with the mid sacrum of the hip area of the patient and passes a second location on the visual representation of the intraoperative radiographic image data associated with the hip area of the patient;
upon receipt of the user touching a second point corresponding to another area of the patient on the visual representation of the intraoperative radiographic image data on the touch-screen display superimposing a second measuring line onto the displayed visual representation of the intraoperative radiographic image data on the touchscreen display of the computerized device, wherein the second measuring line starts at a third location on the visual representation of the intraoperative radiographic image data and is automatically drawn with a predetermined length;
displaying to the user on the touchscreen display of the computerized device at least one of pelvic tilt and pelvic rotation information associated with the first or second measuring line onto the displayed visual representation of the intraoperative radiographic image data; and
repeating a step of receiving intraoperative radiographic image data pertaining to the patient and pertaining to a subsequent surgical placement of the prosthetic hip implant during the surgery.

14. The method of claim 13, further comprising the step of outputting a visual indication of an intra-operative adjustment to be made to a component based on the adjustment factor to achieve a target component orientation.

15. The method of claim 13, further comprising the step of applying the adjustment factor to an intra-operative leg length measurement and outputting a visual indication of an intra-operative adjustment to be made to the patient to achieve a target leg length measurement.

16. The method of claim 13, wherein the step of scoring a first two-dimensional projection occurs before or during the rendering of one or more subsequent two-dimensional projections.

17. The method of claim 13, wherein each of the plurality of two-dimensional projections is rendered before scoring any two-dimensional projection.

18. The method of claim 13, wherein the bony edge contour of the intra-operative imaging information is identified using one of a canny edge detector algorithm, a shape-based segmentation algorithm, manual selection, and a combination thereof.

19. The method of claim 13, wherein the three-dimensional model of the first portion of the patient is generated by applying one of a region grow algorithm, a water shed algorithm, an active contour algorithm, and a combination thereof to the data set of imaging information.

20. An imaging system for intra-operatively positioning a component, comprising:
a computerized display system including a display, a receiver, and a microcontroller operatively coupled to the display and to the receiver and having access to system memory, the system memory including software instruction causing the microcontroller to perform the steps of:

receiving a data set of imaging information representing at least a first portion of a patient in a neutral position;

generating a three-dimensional model of the first portion of the patient based on the data set of imaging information;

receiving intra-operative imaging information representing the first portion of the patient;

identifying a bony edge contour in the intra-operative imaging information;

iteratively rendering a plurality of two-dimensional projections from the three-dimensional model, each two-dimensional projection having a corresponding spatial orientation;

scoring each two-dimensional projection by calculating the distance of the bony edge contour in the intra-operative imaging information to a corresponding contour in each two-dimensional projection;

identifying a global minimum score;

outputting a transformation matrix for the two-dimensional projection having the global minimum score, the transformation matrix representing the orientation of the three-dimensional model relative to the neutral position when the two-dimensional projection having the global minimum score was rendered;

calculating an adjustment factor based on the transformation matrix;

outputting to the display a visual indication of an intra-operative adjustment to be made to a component based on the adjustment factor to achieve a target component orientation displaying a visual representation of the intraoperative radiographic image information on an electronic display of the computer device;

providing by the surgical workflow program a first graphical interface tool to the user on the electronic display that allows the user to mark the visual representation of the radiographic image information on the electronic display, and upon receipt of the user marking the visual representation of the radiographic image information, superimposing a reference line onto the displayed visual representation of the radiographic image information on the electronic display;

providing by the surgical workflow program a second graphical interface tool to the user on the electronic display that superimposes a measuring line corresponding to the reference line onto the displayed visual representation of the radiographic image information on the electronic display, the measuring line having a predetermined parameter based upon receipt of a selection on the second graphical interface tool;

displaying to the user on the electronic display measurement information associated with the measuring line corresponding to the reference line;

wherein the displayed measurement information pertains to a surgical adjustment for the surgery with respect to at least one of: (i) the prosthetic implant and (ii) anatomical components of the patient associated with the prosthetic implant;

receiving a second intraoperative radiographic image information pertaining to the patient and pertaining to an adjusted surgical placement of the prosthetic implant during the surgery; and displaying a visual representation of the second intraoperative radiographic image information on the electronic display of the computer device to confirm whether an adjustment of the patient and the adjusted surgical placement of the prosthetic fall within a desired range.

21. The system of claim 20, wherein the bony edge contour of the intra-operative imaging information is identified using one of a canny edge detector algorithm, a shape-based segmentation algorithm, manual selection, and a combination thereof.

22. A method for intra-operatively positioning a component comprising the steps of:

receiving a data set of imaging information representing a portion of a patient in a neutral position;

generating a three-dimensional model of the portion of the patient from the data set receiving an intra-operative image of the portion of the patient;

rendering a plurality of two-dimensional projections from the three-dimensional model;

identifying a best-fit two-dimensional projection to the intra-operative image;

calculating an adjustment factor by comparing a difference in orientation of the three-dimensional model at a neutral position and the three-dimensional model at the orientation corresponding to the best-fit two-dimensional projection;

displaying a visual representation of the intraoperative radiographic image on an electronic display of the computer device;

providing by the surgical workflow program a first graphical interface tool to the user on the electronic display that allows the user to mark the visual representation of the radiographic image on the electronic display, and upon receipt of the user marking the visual representation of the radiographic image, superimposing a reference line onto the displayed visual representation of the radiographic image on the electronic display;

providing by the surgical workflow program a second graphical interface tool to the user on the electronic display that superimposes a measuring line corresponding to the reference line onto the displayed visual representation of the radiographic image on the electronic display, the measuring line having a predetermined parameter based upon receipt of a selection on the second graphical interface tool;

displaying to the user on the electronic display measurement information associated with the measuring line corresponding to the reference line;

wherein the displayed measurement information pertains to a surgical adjustment for the surgery with respect to at least one of: (i) the prosthetic implant and (ii) anatomical components of the patient associated with the prosthetic implant;

receiving a second intraoperative radiographic image pertaining to the patient and pertaining to an adjusted surgical placement of the prosthetic implant during the surgery; and displaying a visual representation of the second intraoperative radiographic image on the electronic display of the computer device to confirm whether an adjustment of the patient and the adjusted surgical placement of the prosthetic fall within a desired range.

23. The method of claim 22, further comprising a step of reorienting the visual representation of the intraoperative radiographic image on the touchscreen display upon receipt of a manipulation of the touchscreen display by the user.

* * * * *